United States Patent
Miller et al.

(10) Patent No.: US 11,363,997 B1
(45) Date of Patent: Jun. 21, 2022

(54) ELECTRODE PADS FOR BIOIMPEDANCE

(71) Applicant: Halo Wearables, LLC, Morgan, UT (US)

(72) Inventors: David Miller, Morgan, UT (US); Jeffrey Lee, Morgan, UT (US); Devin Miller, Morgan, UT (US)

(*) Notice: Subject to any disclaimer, the term of this patent is extended or adjusted under 35 U.S.C. 154(b) by 85 days.

(21) Appl. No.: 17/031,784

(22) Filed: Sep. 24, 2020

Related U.S. Application Data

(63) Continuation of application No. 16/365,191, filed on Mar. 26, 2019, now abandoned.

(51) Int. Cl.
| | |
|---|---|
| *A61B 5/00* | (2006.01) |
| *G08B 21/02* | (2006.01) |
| *A61B 5/0537* | (2021.01) |
| *G08B 21/18* | (2006.01) |

(52) U.S. Cl.
CPC ............ *A61B 5/746* (2013.01); *A61B 5/0537* (2013.01); *A61B 5/4875* (2013.01); *A61B 5/681* (2013.01); *A61B 5/742* (2013.01); *G08B 21/02* (2013.01); *G08B 21/182* (2013.01)

(58) Field of Classification Search
CPC ..... A61B 5/746; A61B 5/0537; A61B 5/4875; A61B 5/1118; A61B 5/681; A61B 5/724; A61B 2562/0219; G08B 21/02; G08B 21/182
See application file for complete search history.

(56) References Cited

U.S. PATENT DOCUMENTS

| | | | | |
|---|---|---|---|---|
| 2007/0048224 A1* | 3/2007 | Howell | ............... | A61B 5/6802 |
| | | | | 424/9.1 |
| 2011/0172504 A1* | 7/2011 | Wegerich | ............. | A61B 5/7264 |
| | | | | 600/301 |
| 2019/0246976 A1* | 8/2019 | Howell | ............... | A61B 5/4875 |

\* cited by examiner

*Primary Examiner* — Omeed Alizada
(74) *Attorney, Agent, or Firm* — Miller IP Law, LLC

(57) ABSTRACT

A method, system, apparatus, and/or device that may include: a housing, a sensor interface, and a processing device. The housing may be shaped to be affixed to a body of a user and may include an inner cavity that houses electronic components and an impedance sensor. The impedance sensor may include a first contact terminal and a second contact terminal. The sensor interface may be configured to: generate an electric signal; receive the electric signal through a skin layer below a surface of the body of the user; and determine an impedance measurement between the first contact terminal and the second contact terminal based on the electric signal. The processing device may be configured to determine, based on the impedance measurement: a condition of a vascular system of the user; an amount of a constituent of the vascular system of the user; or a hydration condition of the user.

18 Claims, 20 Drawing Sheets

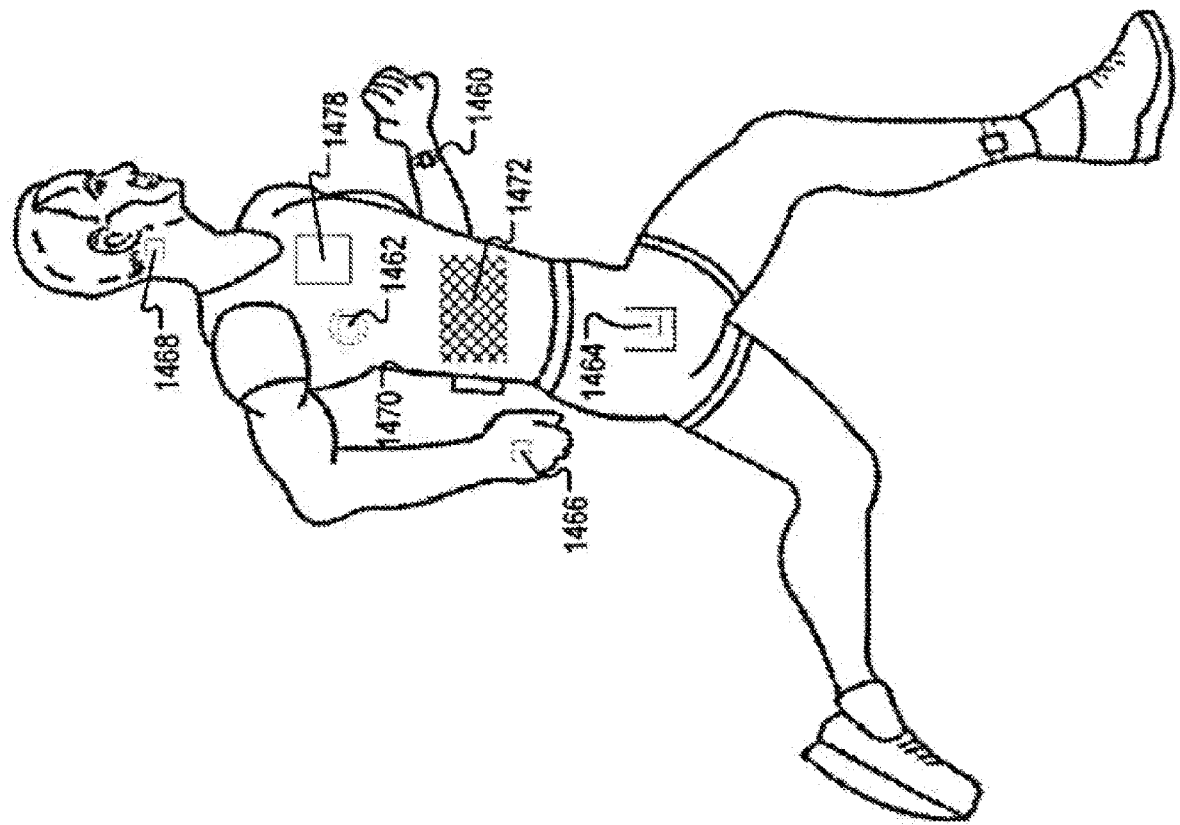
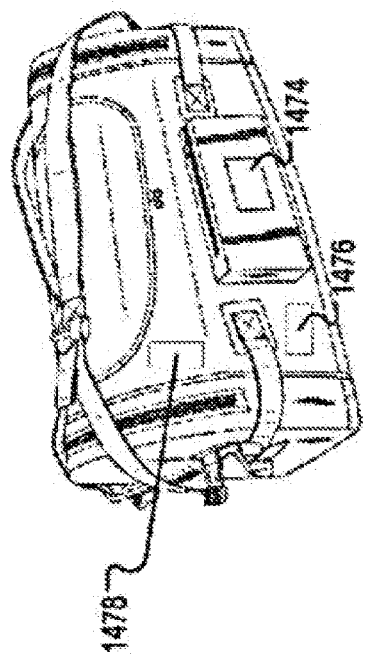
FIG. 14

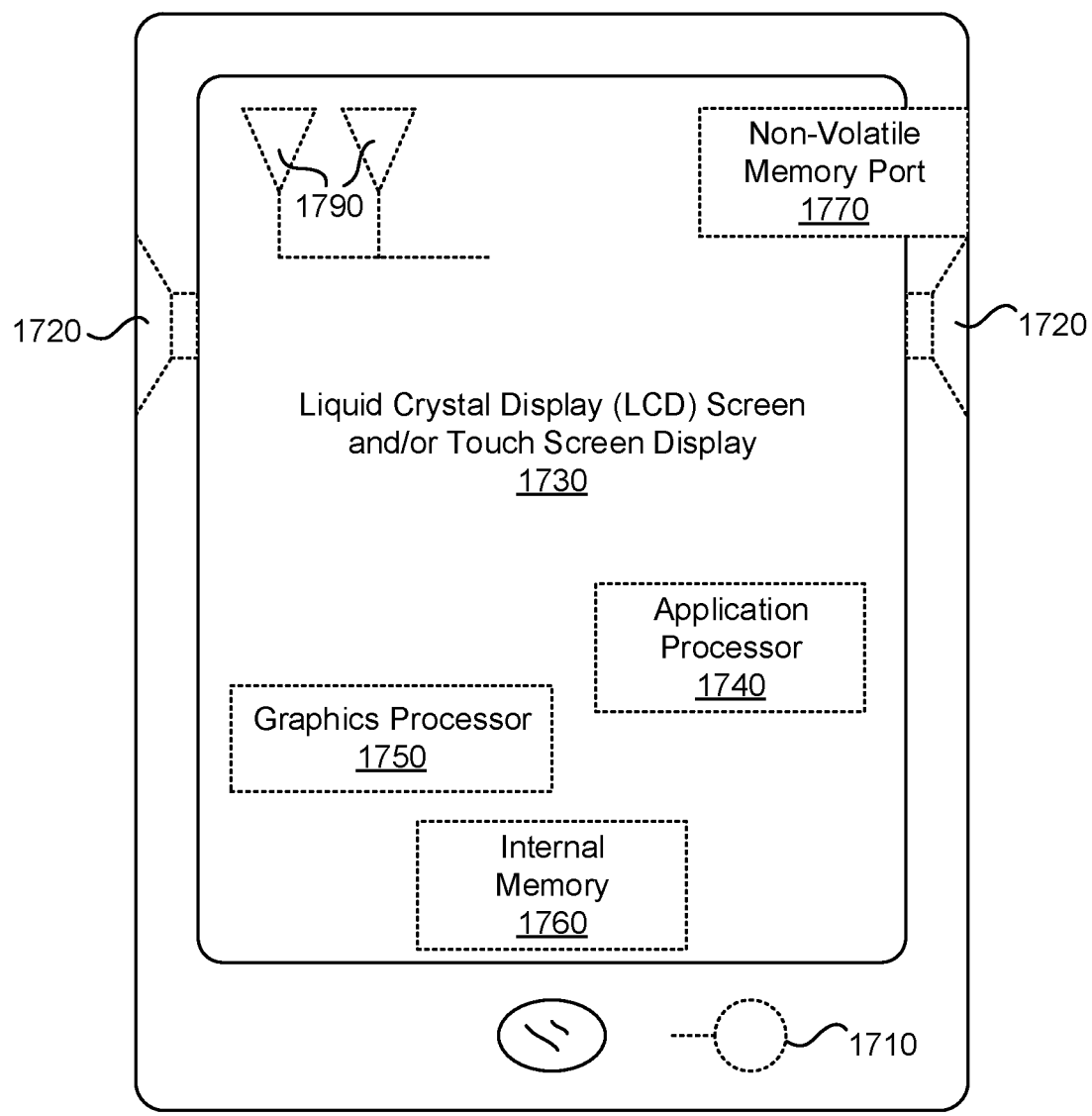
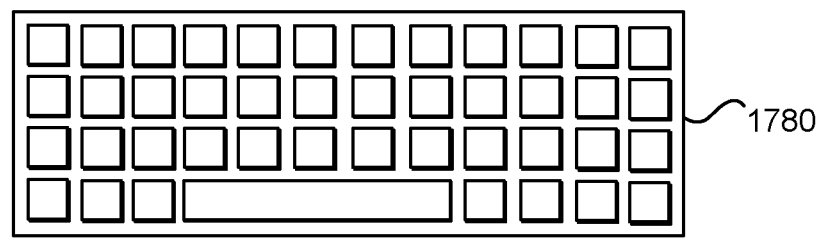
FIG. 17

ELECTRODE PADS FOR BIOIMPEDANCE

CROSS-REFERENCE TO RELATED APPLICATIONS

This application claims the benefit of U.S. Non-Provisional patent application Ser. No. 16/365,191 filed Mar. 26, 2019, which claims the benefit of U.S. Provisional Application No. 62/117,282, filed Feb. 17, 2015 and U.S. Provisional Application No. 62/192,932, filed Jul. 15, 2015, the entire contents of which are incorporated by reference.

BACKGROUND

Dehydration is a condition in which water in a living body decreases below the individual's normal functioning level. Dehydration often occurs when an individual is exerting energy for extended periods of time, an individual intakes little or no water, or the temperature rises to a point where an individual cannot excrete enough sweat to maintain their normal body temperature. Persons that regularly exert themselves in low humidity and/or high temperature conditions and/or for extended periods of time are prone to experience dehydration or dehydration symptoms. Elderly persons and children are also especially prone to experience dehydration or dehydration symptoms.

When a person experiences a dehydrated condition, the individual's ability to perform tasks may begin to deteriorate. For example, in the case of long distance endurance athletes, an individual that becomes dehydrated by loss of as little as 2% body weight may begin to have their performance impaired. Losses in excess of 5% of body weight can decrease the capacity of an individual to perform a task by as much as 30%.

BRIEF DESCRIPTION OF THE DRAWINGS

The disclosure will be understood more fully from the detailed description given below and from the accompanying drawings of various embodiments of the disclosure. The drawings, however, should not be taken to limit the disclosure to the specific embodiments, but are for explanation and understanding only.

FIG. 14 depicts body area network (BAN) devices communicating using a BAN, according to one embodiment.

FIG. 17 provides an example illustration of a processing device disclosed herein, such as a user equipment (UE), a base station, an electronic device (UMD), a mobile wireless device, a mobile communication device, a tablet, a handset, or other type of wireless device, according to one embodiment.

DESCRIPTION OF EMBODIMENTS

Figure 1:
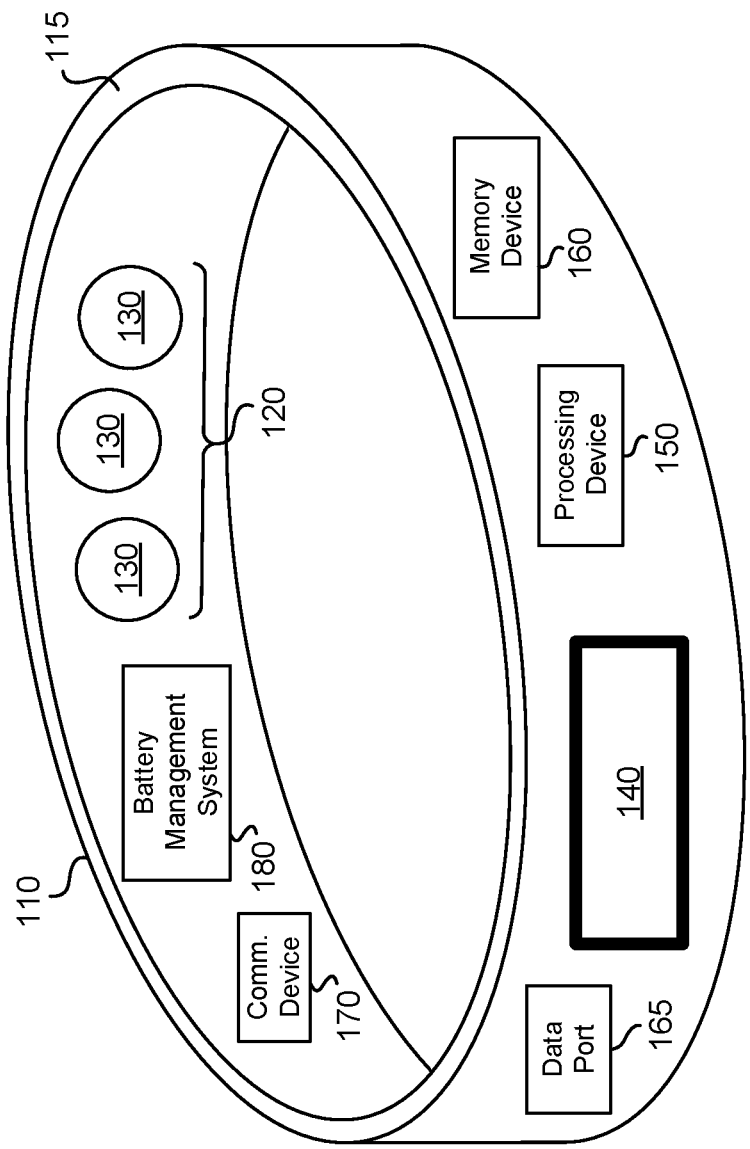
FIG. 1 depicts an electronic device, according to one embodiment.

Contemporary methods of determining the hydration level or fluid balance of an individual include measuring body weight changes of an individual over a period of time and urinalysis. One crude way of monitoring an individual's fluid balance is to monitor how the body weight of the individual changes over a short period of time. Using this method, taking a body weight measurement each morning can show a pattern of hydration over time. The same method can be applied to determine how much sweat an athlete excreted while exercising by weighing the athlete before and after exercise.

Urinalysis can also be used to determine moderate changes in an individual's fluid balance. A simple approach to urinalysis is to analyze the color of the individual's urine to determine their hydration level. More scientific urinalysis tests such as urine specific gravity and urine osmolality can be used for a more accurate measurement of an individual's fluid balance.

However, urinalysis and tracking an individual's body weight changes overtime are invasive procedures that fail to give the individual real time information regarding the individual's changing hydration condition. Thus, it is desirable that an individual's hydration level is monitored regularly and any dehydration is detected in the early stage before an individual's performance levels are impacted or before they reach a serious dehydration condition.

The embodiments described herein address the above noted deficiencies by determining a hydration condition of a user using bioelectrical impedance. Bioelectric impedance measures the resistance of body tissues to the flow of an electric signal. Electric signals flow more easily through parts of the body that have high concentrations of fluids such as blood, urine, and muscle. Moreover, as skin becomes wet, an impedance of the skin decreases and electric signals between bioelectric impedance sensors can flow through the skin at a greater rate.

The human skin is composed of multiple skin layers. The top layer of skin, the epidermis, is responsible for making new skin cells, giving skin its color and protecting the body. Under the epidermis layer is the dermis layer. The dermis layer among other functions produces sweat. Sweat is developed in the dermis layer and travels through skin pores to reach the surface of the body. In one example, an electric signal traveling through the dermis layer will encounter less impedance as the body perspires because sweat, a relatively conductive substance in a human body, will allow the electric signal to flow at a lower impedance level than other substances of in the body. Thus, by measuring an impedance of an electric current that has traveled through the dermis layer, a hydration condition of an individual can be determined. Alternatively, an impedance measurement can be taken in the epidermis or other layer of the skin where sweat is also present.

In one embodiment, an electronic device can be used to measure a bioelectrical impedance level of an individual. The electronic device can include a housing having an outer surface with a first side of the housing and a second side of the housing. In one embodiment, the first side of the housing can be an underside of the housing that is shaped to be affixed to body of a user. The housing can include an inner cavity to house electronic components, as discussed in greater detail in the proceeding paragraphs. The housing may have a first cavity and a second cavity on the outer surface of the housing. In one embodiment, the housing can have multiple cavities on an outer surface. For example, the housing may have a first cavity and a second cavity on the underside of the outer surface of the housing. In one embodiment, a cavity can be an indentation or a pit on an inner surface or outer surface of the housing. In another embodiment, a cavity is a channel that extends from the outer surface of the housing to the inner cavity of the housing. Components of the electronic device may be disposed into various channels or recesses located on the housing. For example, a first impedance pad may be disposed in a recess or channel of the outer surface of the housing. The impedance pad can be connected to one of the electronic components in the inner cavity via a connector that is disposed in a channel of the housing.

In one embodiment, the electronic device has an impedance sensor having a first contact terminal and a second contact terminal. In one embodiment, a contact terminal may be an impedance pad, electrode, conductive material, or the like. In one embodiment, a first end of the first contact terminal is flush with the outer surface of the housing and may be operable to transmit an electric current into the body of a user. In another example, the first contact terminal may be disposed into a recess of the housing such that the first contact terminal does not extend beyond the surface of the housing when the device is worn by the user. In still another example, the first contact terminal may extend beyond the surface of the housing for increased contact with the skin when the device is worn by the user.

In one embodiment, the electric signal transmitted from the first impedance pad may include an electric signal transmitted at discrete frequencies. In another embodiment, the electric signal transmitted from the first impedance pad may be a spectrum of frequencies between 1,000 hertz (Hz) and 100,000 Hz. In one example, the sensor interface may measure the impedance at multiple frequencies of the spectrum of frequencies to determine the hydration condition of the user. In another example, the sensor interface may measure the impedance across a portion of the spectrum of frequencies or the entire spectrum of frequencies to determine the hydration condition of the user.

In another embodiment, the electronic device may take a full spectrum of measurements over a range of frequencies. For example, the electronic device may take a full spectrum of measurements over a range of 1,000 Hz to 100,000 Hz. These measurements can be taken over a continuous period of time or periodically. In one example, the sensor interface may determine if any of the frequencies of the spectrum of frequencies have changed over one or more measurements. In this example, the first impedance pad may emit a frequency range of 1,000 Hz to 100,000 Hz into the body. In this example, the second impedance pad may take continuous measurements over the entire frequency range to determine if any of the frequencies have changed from previously taken measurements. In another embodiment, the electronic device may take measurements at n number of discrete frequencies over a period of time. In one example, n may be 10. In another example, n may be 50 or 100.

In one example, an electric signal with a frequency between 50,000 Hertz (Hz) and 100,000 Hz may pass through bodily tissue with less impedance than an electric signal with a frequency between 1,000 Hz and 49,000 Hz.

In one embodiment, the second contact terminal of the impedance sensor may be disposed in a recess of the second cavity of the housing. In one example, the second contact terminal may have a first end of that is flush with the outer surface of the housing and may receive a portion of the electric current from a depth below the surface of the body. In still another example, the second contact terminal may extend beyond the surface of the housing for increased contact with the skin when the device is worn by the user. The contact terminal is at a fixed distance from the second contact terminal to measure an impedance at a depth below the surface of the body, as described in greater detail in the proceeding paragraphs.

In another embodiment, the electronic device may have a sensor interface coupled to the impedance sensor. The sensor interface may receive, from the second contact terminal, a portion of the electric current sent from the first impedance pad. The electric current may flow between the first contact terminal and the second contact terminal through a skin layer that is below the surface of the body. The sensor interface may further determine an impedance measurement between the first contact terminal and the second contact terminal using the portion of the electric current received at the second contact terminal.

In another embodiment, electronic device may have a processing device coupled to the sensor interface and the impedance sensor. In one example, the processing device can compare a current impedance measurement to a previous impedance measurement and determine a change in an impedance level of the body using the impedance measurement, as discussed in greater detail in the proceeding paragraphs. In another example, the processing device can determine a hydration condition of the body by comparing the change in the impedance level from a plurality of impedance measurements, as described in greater detail in the proceeding paragraphs.

FIG. 1 illustrates an electronic device 110, according to one embodiment. FIG. 1 illustrates that the electronic device 110 can be a wearable device such as a wristband, a headband, an armband, a chest band, a leg band, an ankle band, a strap, a garment or piece of clothing (such as a hard hator shirt), an accessory, or other object that can be shaped to attach or couple to an user. The electronic device 110 can also be integrated into other wearable objects such as a hard hat, a safety harness, a safety lock out, shoes, a bag, and so forth. Alternatively, the electronic device may be an implantable device that may be implanted under the skin of the user.

In one example, the electronic device 100 can be located in an area that is practical for the individual to wear the electronic device 110 for an extended period of time, such as a 24-hour period. For example, as many individuals are accustom to wearing wristwatches, a comfortable location for the individual to wear the electronic device 110 for an extended period of time may be at the wrist location. In another example, the electronic device may be located at a location on the individual that will provide a high measurement accuracy level, such as a location on the individual that is the most sensitive to a selected physiological measurement. For example, the chest, wrist, tip of the finger, or ear lobe may be locations that are sensitive to taking physiological measurements and the electronic device 110 can be shaped to attach to the individual at chest, wrist, tip of the finger, or ear lobe locations.

In one embodiment, the electronic device 110 may include a housing 115 with one or more inner cavities. The one or more cavities can include space to house: a sensor array 120, a sensor 130, a display 140, a processing device 150, a memory device 160, a communication device 170, and/or a battery management system (BMS) 180. In one embodiment, the housing 115 can be hermetically sealed, e.g., airtight, water proof, sweat proof, dust proof, and so forth. In another example, the housing can be a unibody (e.g., a single unit), where components such as the sensor 130 can be sealed within the unibody. In another embodiment, the housing 115 can include multiple pieces, such as a first housing piece and a second housing piece, that are sealed together to form a hermetically sealed housing 115.

In one example, the electronic device 110 can be an invasive device attachable to (or implantable within) a body of a user to obtain an invasive physiological measurements from the user. In another example, the electronic device 110 can be a non-invasive device attachable to the body of the user to obtain non-invasive measurements from the user.

The electronic device 110 can include a sensor 130 or sensor array 120 that can be integrated into the electronic device 110. In another example, the sensor 130 or the sensor array 120 can be coupled to the processing device 150 of the hydration monitoring device. 110. In one example, the sensor 130 can be a physiological sensor. The physiological sensor can include an impedance sensor, an optical sensor, an electrocardiography (ECG) sensor, a fluid level sensor, an oxygen saturation sensor, a body temperature sensor (skin temperature or core temperature), a plethysmographic sensor, a respiration sensor, a breath rate sensor, a cardiac sensor, a bio-impedance sensor, a spectrometer, a heart rate sensor, a blood pressure sensor, a pulse oximeter, or other physiological sensors. In another example, the sensor 130 can be a Newtonian sensor. The Newtonian sensor can include: a two dimensional (2D) accelerometer, a three dimensional (3D) accelerometer, a gyroscope, a magnetometer, a vibration sensor, a force sensor, a pedometer, a strain gauge, and so forth. In another example, the sensor 130 can be a location sensor. The location sensor can include: a global positioning system (GPS); a triangulation system; and so forth. In another example, the sensor 130 can be an environmental sensor. The environmental sensor can include: a humidity sensor, an ambient temperature sensor, an altitude sensor, a barometer, a weather sensor, and so forth. In one embodiment, the sensor 130 can be a non-invasive sensor. In one embodiment, one or more of the physiological sensors, the Newtonian sensors, or the environmental sensors can be integrated into the electronic device 110 or physically coupled to the electronic device 110. In another example, one or more of the physiological sensors, the Newtonian sensors, or the environmental sensors can be physically separate from the electronic device 110 and can be communicate data with the electronic device, either directly or indirectly as discussed herein.

In one embodiment, the electronic device 110 can include a display 140 to show information to a user or a third party based on the measurements from the sensor 130 or the sensor array 120. In one embodiment, the display 140 can show the time, e.g., a clock. In another embodiment, the information shown on the display 140 may include measurement information, such as: a light backscatter measurement, a heart rate of an individual, a breathing rate of the individual, a blood pressure of the individual, and so forth. In another example, the information shown on the display 140 may include recommendations, such as: a recommendation to take a break; a recommendation to go home; a recommendation to go to a hospital; or other recommendations. In another example, the information shown on the display 140 may include alerts, such as: an alert that a user may be experiencing a dehydration condition; an alert to take medication; an alert that an environment may not be safe; an alert that the user has fallen down; or other alerts. In another example, the information shown on the display 140 may include: hydration information, health status information, and other information.

In another embodiment, the display 140 can display information to a user or a third party based on information from other devices in communication with the electronic device 110. For example, the electronic device 110 can receive information from an automobile or a smart home device of a user or a third party. In this example, the information from the automobile or the smart home device can include ambient temperatures, humidity information, weather information, and so forth. The electronic device 110 can display the information from the automobile or the smart home device or use it in combination with measurements taken using the sensor 130 or the sensor array 120 to determine and display other information, such as a hydration level of the user.

In another embodiment, the processing logic of the electronic device 110 can determine an error with the sensor 130 or the sensor array 120 and display the error to the user or the third party using the display 140. For example, the processing logic can determine that the sensor 130 or the sensor array 120 is not interfacing with the user properly and the processing logic can use the display 140 to display an error message to the user. In one embodiment, the sensor 130 or the sensor array 120 is not interfacing with the user properly when the sensor 130 or the sensor array 120 is only partially contacting the body of the individual or is not completely contacting the body of the individual. In another embodiment, the sensor 130 or the sensor array 120 is not interfacing with the user properly when an object or particle is interfering with processing logic using the sensor 130 or the sensor array 120 to take physiological measurements of the user, environmental measurements, or other measurements. In one example, processing logic can determine that objector particle is interfering with taking measurements when measurement information is outside a defined measurement range or there is a discontinuity in the measurement information that exceeds a threshold level for the discontinuity. For example, when dirt comes between the sensor 130 or the sensor array 120 and the body of the user, the dirt can cause a discontinuity in the measurement information. When the processing logic determines the discontinuity in the measurement information, the processing logic can use the display 140 to display an error message associated with the discontinuity.

In another embodiment, the sensor 130 or the sensor array 120 is not interfacing with the user properly when the electronic device 110, the sensor 130, or the sensor array 120 has become dislocated or displaced. For example, measurements taken using the sensor 130 or the sensor array 120 with a first orientation can have a higher accuracy level than measurements taken using the sensor 130 or the sensor array 120 with a second orientation. In one example, the first orientation is an orientation where the user is wearing the electronic device 110 in a correct orientation and the second orientation is an orientation when the electronic device 110 has slipped or shifted to a different orientation. When the electronic device 110 has slipped or shifted the second orientation, the processing logic identifies that a measurement is outside a defined measurement range or there is a discontinuity in measurement information and uses the display 140 to display an error message associated with slippage or shifting.

In one example, the display 140 can be a touch screen display, such as a capacitive touch screen or a resistive touch screen. In another example, the display 140 can display a graphical user interface (GUI) to receive information. In another example, the electronic device 110 can include a data port 165, such as a universal serial bus (USB) port, a mini-USB port, a micro-USB port, a LIGHTNING® port, and so forth. In another example, the electronic device 110 can include a wireless communications device 170 (as discussed in the proceeding paragraphs) to send or receive information. The electronic device 110 can include a processor or processing device 150 to analyze or process measurements, received information, user input data, and/or other types of data.

In one example, the electronic device 110 can monitor stress on a respiratory system of the individual. For example, the electronic device 110 can use the sensor 130, such as an oxygen saturation sensor, to monitor the stress on a respiratory system of the individual.

In another example, the electronic device 110 can use one or more sensors 130 in the sensor array 120 to monitor stress on a plurality of systems of an individual, such as a biological system or a body system. The biological system may include a respiratory system, a cardiovascular system, a nervous system, an integumentary system, a urinary system, an excretory system, a digestive system, an immune system, an endocrine system, a lymphatic system, a muscular system, a skeletal system, a reproductive system, and other systems. The body system may include two or more organs working together in the execution of a specific bodily function, e.g., a neuroendocrine system, a musculoskeletal system, etc. For example, the electronic device 110 can monitor stress on the cardiac system of an individual using a blood pressure sensor of the sensor array 120 and can monitor the stress on the respiratory system of the individual using an oxygen saturation sensor of the sensor array 120.

In another example, the electronic device 110 can monitor biological systems, organs, body parts, body system, or other areas of an individual. In another example, the electronic device 110 can monitor or aggregate stress measurements from the sensors of the sensor array with other measurements, such as a lung capacity of an individual, a hematocrit (HCT), an oxygen saturation level, and/or or other medical measurements. In another example, the electronic device 110 can analyze the aggregated measurements to determine stress on one or more biological systems, organs, body parts, and/or body system and use the aggregated measurements to determine medical, health, and/or safety conditions.

In one example, the electronic device 110 can use the sensor array 120 to monitor a medical condition of an individual, such as a cardiac condition, under various environments or conditions for continuous, semi-continuous, or a periodic period of time on a long-term or protracted basis. In one example, sensor measurements can be collected using the sensor 130 in the sensor array 120 of the electronic device 110. In another example, the sensor measurements can be stored on anon-tangible computer readable medium device 160 (e.g., a memory device) coupled to the electronic device 110 or in communication with the electronic device 110.

In one embodiment, the battery management system (BMS) 180 can include: one or more batteries (such as a rechargeable battery), a charger, and a management device. The management device can manage and control power, e.g., power to and from the one or more batteries or regulate power of the electronic device 110. For example, the management device can direct power received from an external power source, such as wall outlet, via the data port 165 (e.g., a USB port) and can recharge the one or more batteries. In another example, the BMS 180 can include a wireless power system with a wireless power coil to receive power. In this example, the management device can direct power received via the wireless power system to the one or more batteries. In another example, the management device can direct power to components or systems of the electronic device 110, such as the sensor array 120, the sensor 130, the display 140, the processing device 150, the memory device 160, and/or the communication device 170. In one example, the management device can be a processor or another processing device, independent of the processing device 150, that can manage and control the power. In another example, the management device can be software executed by the processing device 150 or processing logic to manage the power.

In one embodiment, the BMS 180 can determine when a charge level the one or more batteries is below a threshold amount and can send a notification to the user indicating that the electronic device 110 needs to be charged. In one example, the electronic device can send the notification to the user using a sensory device such as a vibrator, a speaker, a display, and so forth.

Figure 2A:
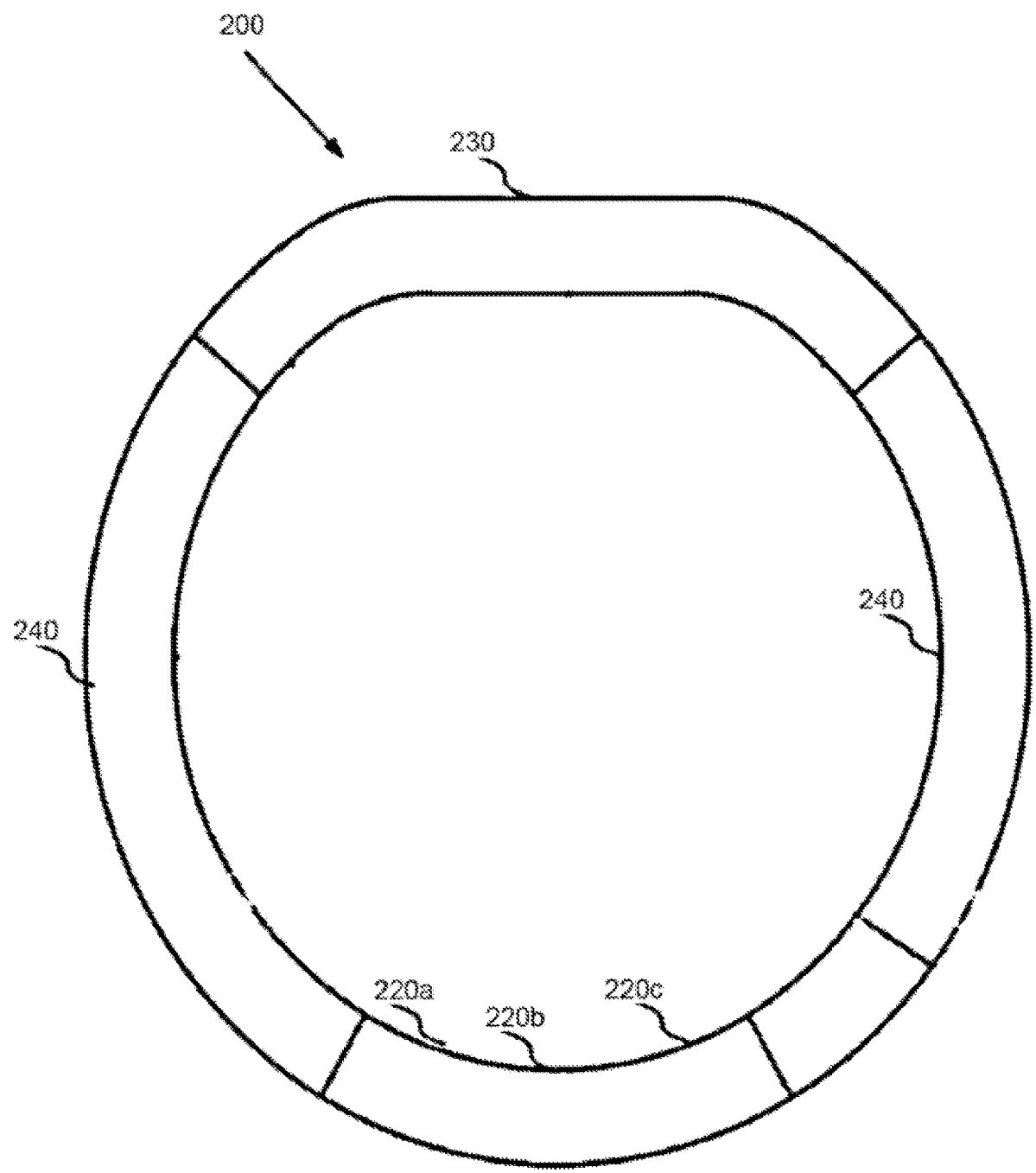
FIG. 2A depicts a side view of an electronic device, according to one embodiment.

FIG. 2A illustrates a side view of an electronic device 200, according to one embodiment. The electronic device 200 can include one or more integrated sensors 220. In one exemplary embodiment, the electronic device 200 can have a flattop portion 230 and a circular remaining portion 240 to fit to the contour or shape of a wrist on a user. An advantage of the electronic device 200 fitting to contours of the wrist can be to align the sensors 220 of the electronic device 200 with a specific location on the wrist of the individual (such as a bottom, side, or top of the wrist). The electronic device 200 may be fit to the contours of the wrist to provide and/or maintain proper contact between the sensor 220 of the electronic device 200 and a body of the user. The location of the sensors 220 is not intended to be limiting. The sensor 220 can be located at different locations on the electronic device 200. Additionally, a shape of the electronic device 200 is not intended to be limiting. The electronic device 200 can be a variety of different shapes, such as oval, circular, rectangular, and so forth.

Figure 2B:
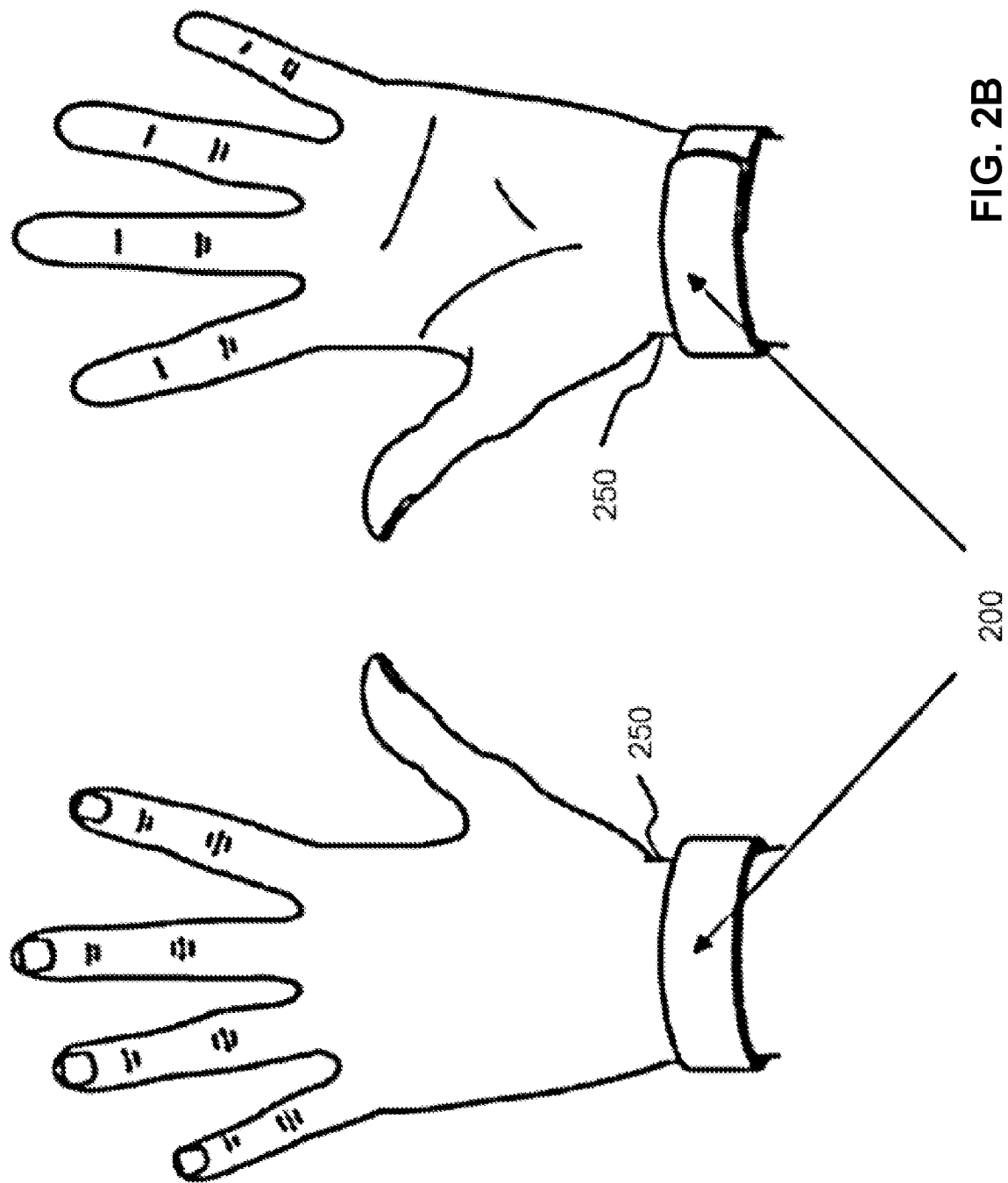
FIG. 2B depicts a top and a bottom perspective of an electronic device attached to a wrist of an individual, according to one embodiment.

FIG. 2B illustrates a top and a bottom perspective of an electronic device 200 attached to a wrist 250 of an individual, according to one embodiment. The electronic device 200 may be located on the wrist of an individual and may take one or more measurements at the wrist location. In one example, the electronic device 200 can cover or wrap around the circumference of the wrist 250 of the individual.

Figure 3:
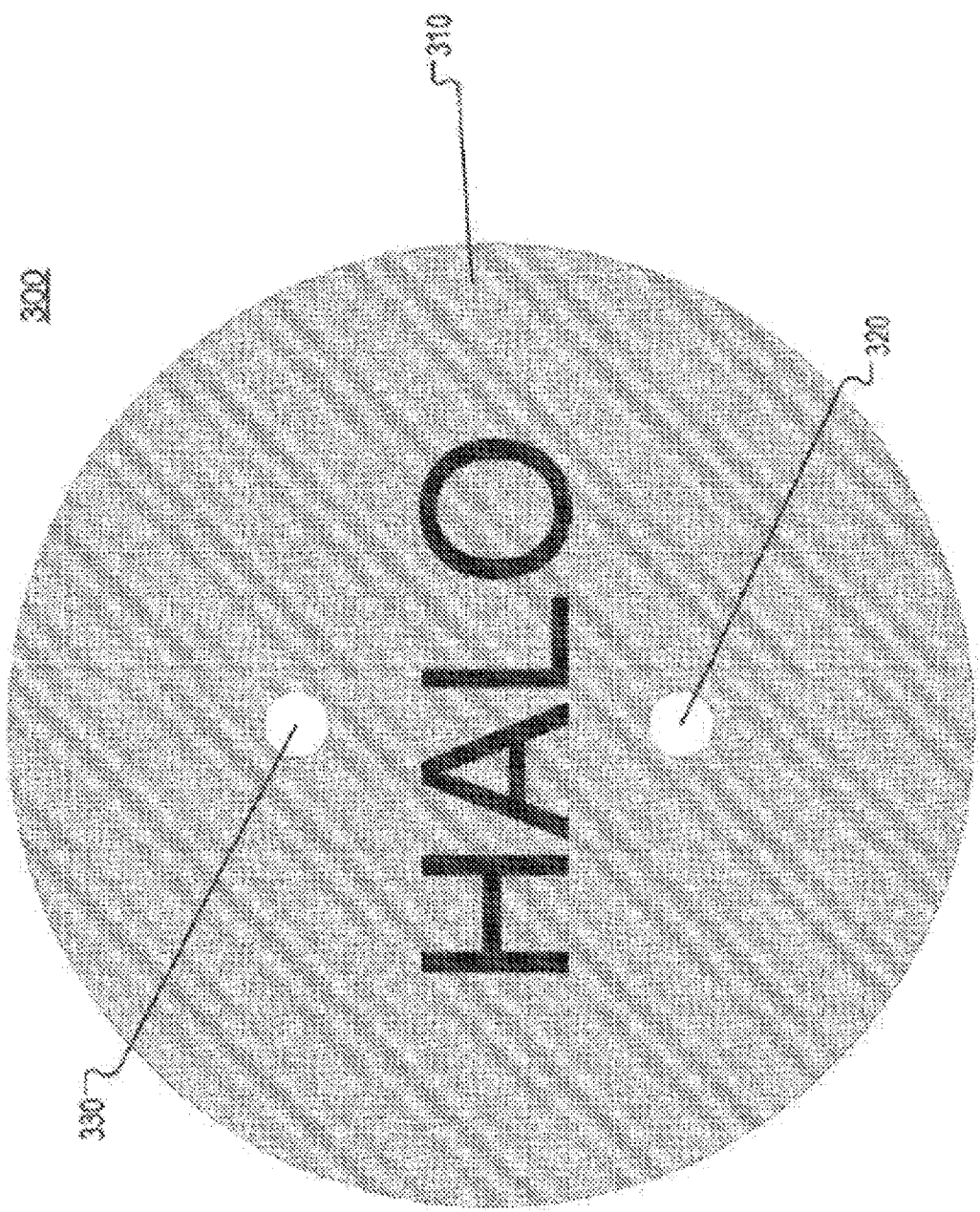
FIG. 3 depicts a top view of the electronic device, according to one embodiment.

FIG. 3 illustrates a top view of the electronic device 300, according to one embodiment. The electronic device 300 may have a display 310. The display 310 may provide information to a user such as indicating the user's hydration condition, temporal information such as the user's hydration condition over time, a time and date, and any information relevant to a user's physiological state. In one embodiment, the display 310 may be a graphical user interface (GUI) that allows a user to interact with the device. In another embodiment, the display may be located on an external device, such as a cellular telephone, a personal computer, or other mobile device. The electronic device 300 may further include a power indicator 320 to indicate a state of the electronic device 300. In another embodiment, the electronic device 300 may comprise one or more sensors such as a humidity and/or temperature sensor 330. In one embodiment, a humidity sensor may detect the humidity level of the user's environment or a sweat rate of a user. A temperature sensor may detect the temperature of the user's environment or a surface temperature of a user.

Figure 4:
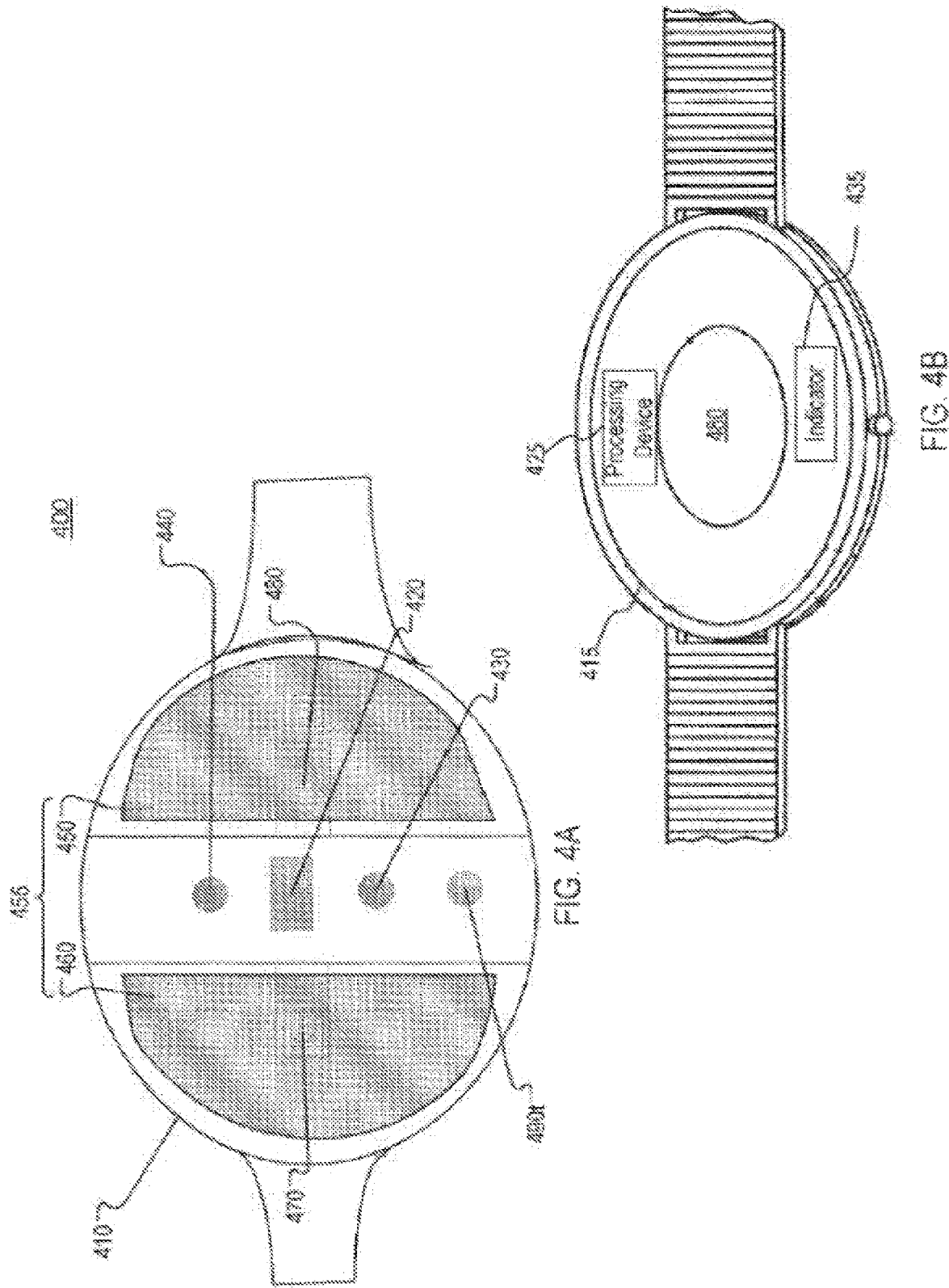
FIG. 4A depicts the underside of an electronic device, according to one embodiment.
FIG. 4B depicts an underside view or interior view of the electronic device, according to one embodiment.

FIG. 4A illustrates the underside of an electronic device 400 is depicted, according to one embodiment. The electronic device 400 includes a housing 410, an optical sensor 420, light sources 430 and 440, an impedance sensor 455 including impedance pads 450 and 460, contact wings 470 and 480, and a humidity and/or temperature sensor 490. The housing 410 of the electronic device 400 may be shaped to affix to the wrist, head, arm, chest, leg, ankle, ear lobe, fingertip, or other surface of the body. The housing 410 may have one or more cavities to house components of the electronic device 400. In one example, electronic device has a cavity 465 to house the second impedance pad 460. As previously discussed, the cavity 465 may be disposed on a location on an outer surface of the housing 410. In this example, the underside of the housing 410 can be along a portion of the outer surface of the housing 410. In one example, the underside of the housing 410 may be the surface of the device that contacts the user when worn. In this example, the cavity 465 may be a channel extending from the underside of the outer surface of the housing 410 to an inner cavity of the housing 410. The contact terminal may be disposed in the channel such that the contact terminal is flush with the plane defined by the outer surface of the housing 410 and is coupled to another component of the electronic device that is disposed in the inner cavity of the housing 410. In other examples, the impedance pad 450, optical sensor 420, humidity and/or temperature port 490, and light sources 430 and 440 are disposed in the cavity 465 or other similar cavities.

The sensor components such as the optical sensor 420, light sources 430 and 440, impedance pads 450 and 460, and humidity and/or temperature sensor 490 may be embedded into the one or more cavities of the underside of the housing 410 of the electronic device 400. In some cases, one or more sensor components may sit flush with a plane defined by an underside of the housing 410. When affixed to a user, the sensor components contact the skin of the user without extending beyond the plane defined by the underside of the housing 410. Alternatively, the sensor components may be recessed into the housing 410. In this example, the sensor components may be recessed into the housing 410 such that the sensor components do not contact the skin of the user when the device is worn by the user. In another example, the sensor components may extend beyond the surface of the housing 410 for increased contact with the skin when the device is worn by the user.

In one embodiment, the electronic device 400 includes impedance sensor 455 having impedance pads 450 and 460. Impedance sensor 455 may be coupled to processing device 425 and sensor interface unit (depicted as 806 in FIG. 8). Moreover, impedance pads 450 and 460 may be coupled to the processing device 425 through contact wings 470 and 480. In one embodiment, processing device 425 or sensor interface unit 806 may cause impedance pad 450 to transmit an electric signal into the body of a user. Impedance pad 460 may operate to receive the electric signal from a skin layer below the surface of the body. In one embodiment, when the skin is perspiring or otherwise wet, the sensor interface 806 will measure less impedance than it would if the user was not perspiring or the skin was otherwise dry. A change in the impedance of the body as measured by the sensor interface 806 taking multiple impedance measurements may indicate that a hydration condition of the body has changed, as discussed in greater detail in the proceeding paragraphs.

The impedance pads 450 and 460 may be embedded into cavities of the housing 410. In one embodiment, the cavities are located on a plane defined by the outer surface of the housing 410. In one example, the impedance pads 450 and 460 may be disposed into a recess of the housing. In one example, the impedance pads 450 and 460 may extend beyond the surface of the housing for increased contact with the skin when the device is worn by the user.

The optical sensor 420 may be embedded into cavity 462 and the light sources 430 and 440 may be embedding into cavities 464 and 466, respectively. Moreover, optical sensor 420 and light sources 430 and 440 may be located between impedance pads 450 and 460. In one embodiment, the light sources 430 and 440 are light emitting diodes (LEDs). In another embodiment, the light sources 430 and 440 may be incandescent light sources, halogen light sources, or the like. Light sources 430 and 440 may emit a full spectrum wavelength of light. In this example, a full spectrum wavelength describes the electromagnetic spectrum from infrared to near-ultraviolet. In another example, the light sources 430 and 440 may emit a discrete wavelength of light into a body corresponding to measurements of potassium, sodium, or other substances in the blood stream or other bodily tissue.

In one embodiment, optical sensor 420 is to detect an intensity of one or more wavelengths of light reflected by bodily tissue of a user. The optical sensor 420 is may be coupled to a processing device and a sensor interface. The sensor interface may receive the detected light from the optical sensor and measure the intensities of wavelengths that have been detected. In one embodiment, the optical sensor 420 is used in concert with other components of the electronic device 400 to determine a hydration condition of the body of a user. The determination can be made by measuring the concentration levels of minerals, such as electrolytes, in the body.

In another embodiment, the electronic device 400 includes a humidity and/or temperature sensor 490. In one example, the humidity and/or temperature sensor 490 may perform a sweat rate measurement to determine an amount the body is perspiring. In another example, the humidity and/or temperature sensor 490 may perform a surface temperature measurement of the skin. In another embodiment, the electronic device 400 may also include a pulse oximeter to measure a user's blood oxygen level.

FIG. 4B illustrates a bottom view of the electronic device 400, according to one embodiment. The electronic device 400 may include a processing device 425 coupled to the sensors 420, 455, and 490 to take selected measurements. The processing device 425 may receive measurement information from the one or more sensors 420, 455, and 490 and analyze the measurement information to determine selected information, such as a hydration condition, physiological information, medical information, and so forth. In one example, the selected information can be hydration condition information, cardiac information (e.g., blood pressure or heart rate), blood oxygen level information, skin luminosity information, or other user information.

The electronic device 400 may also include one or more indicators 435 used to alert the user of the electronic device 400 of a hydration condition change. The indicator 435 may be on the top or the bottom of the electronic device 400 based on a type of the indicator 435. For example, the indicator 435 can be a display or light may be on the top of the electronic device 400. In another example, the indicator 435 can be a vibrator on the bottom of the electronic device 400. In another example, the indicator 435 can be a speaker.

Figure 5:
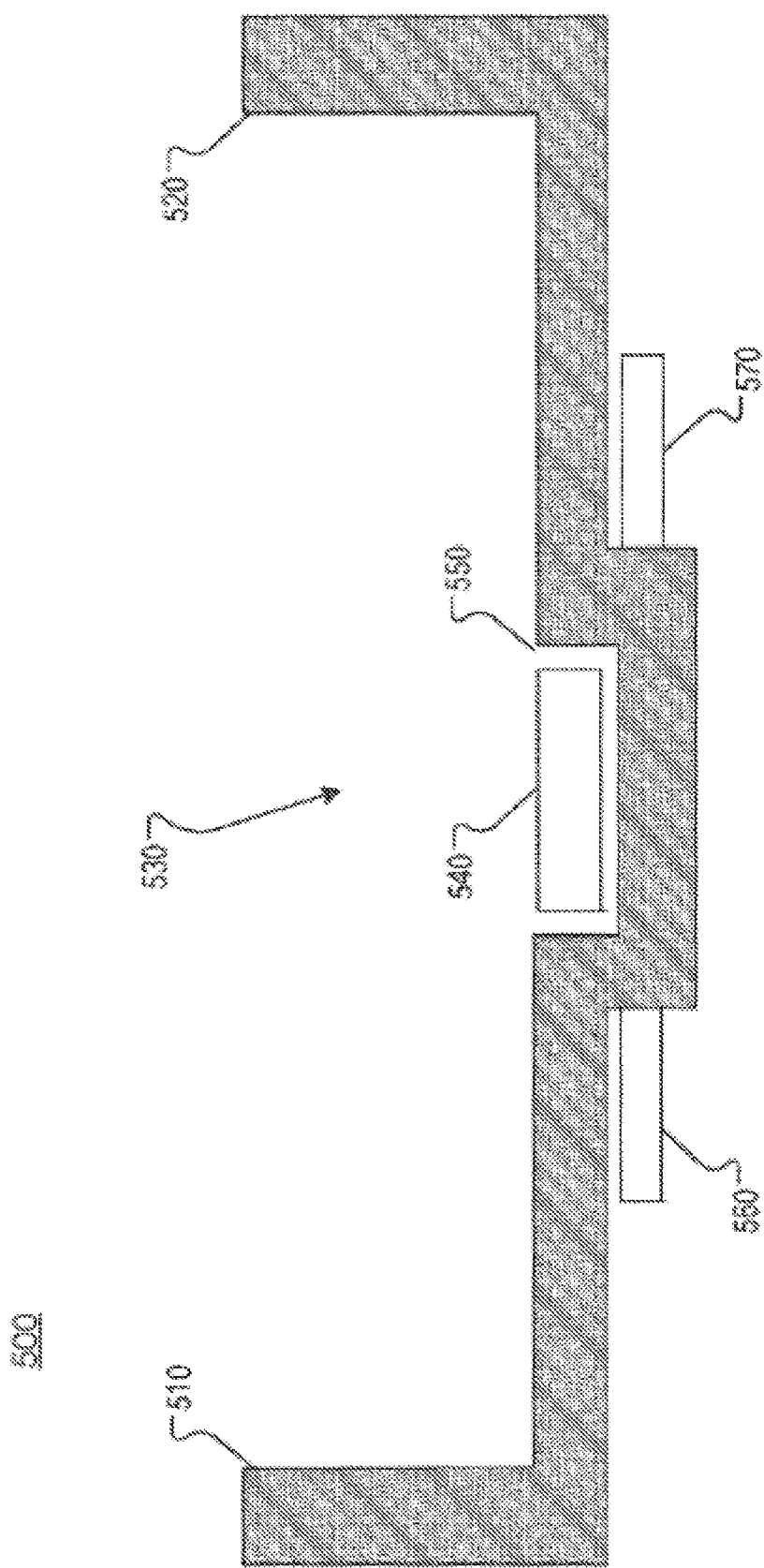
FIG. 5 depicts an exposed side view of the electronic device, according to one embodiment.

FIG. 5 illustrates an exposed side view of the electronic device 500, according to one embodiment. Electronic device 500 includes an inner cavity 530 to house components of the electronic device 500. Inner cavity 530 may be defined by housing walls 510 and 520. In one example, the inner cavity 530 may house at least the processing device 425, the data storage unit 810, and circuit board 540 embedded with one or more sensors.

In one embodiment, circuit board 540 (e.g. circuit board 1180 in FIG. 11) may be disposed into trough 550. In one example, circuit board 540 includes processing device 425 and is coupled to impedance sensor 455 through contact wings 560 and 570.

Figure 6:
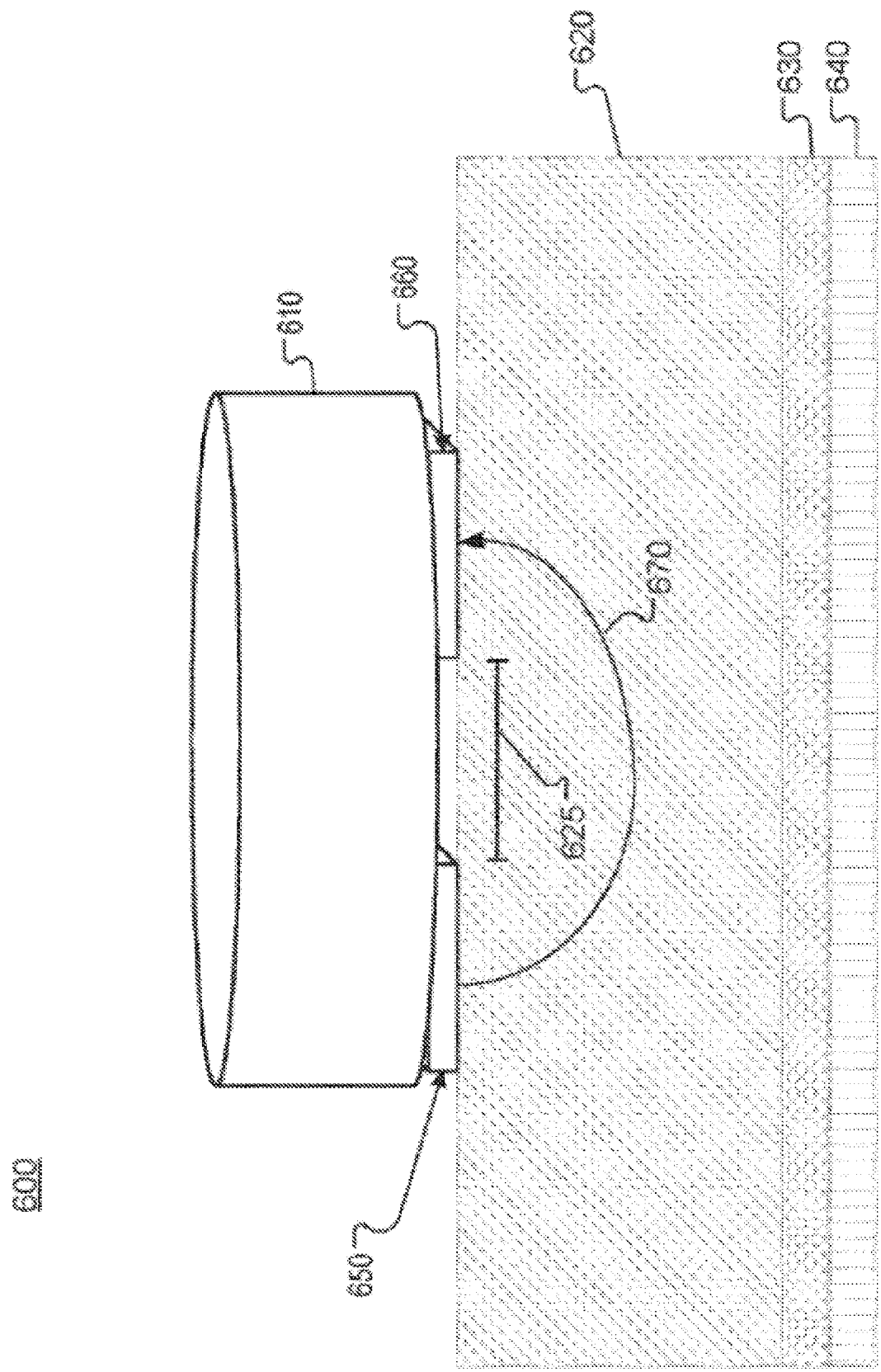
FIG. 6 depicts an electronic device interacting with a user, according to one embodiment.

FIG. 6 illustrates an electronic device 600 interacting with a user, according to one embodiment. Electronic device 600 may include housing 610. Housing 610 may be embedded with impedance pads 650 and 660. The second impedance pad 660 may be separated from the first impedance pad 650 by a fixed distance 625 to measure a portion of the electric signal that has passed through the dermis or epidermis layers of the skin. In one example, sensor interface unit 806 uses impedance pad 650 to transmit an electric signal into the skin of a user. The sensor interface unit 806 uses the second impedance pad 660 to receive electric signals. The second impedance pad 660 may receive a portion of the electric signal transmitted by impedance pad 650.

The level of electricity of the electric signal that is received at the second impedance pad 660 depends in part on the fixed distance 625 between the first impedance pads 650 and the second impedance pad 660. For example, when the impedance measurement is being taken at the wrist, if the impedance pads 650 and 660 are separated by between approximately 1 millimeters (mm) and 4 mm, the second impedance pad 660 will receive a portion of the electric signal that has travelled through a shallow portion of the skin, such as the epidermis layer of the skin. In the same example, when impedance pads 650 and 660 are separated by a fixed distance of approximately 12 mm to approximately 18 mm, the second impedance pad 660 may receive a portion of the transmitted electric signal that has travelled through the dermis layer 620 of the skin. Alternatively, if impedance pad 650 is separated from second impedance pad 660 by a distance of greater than 25 mm, the second impedance pad 660 may not receive the portion of the electric signal or may receive a portion of the electric signal that has been transmitted to a depth below the dermis layer such as a layer of veins 630 or arteries 640 and the measurement may be inaccurate. Blood constituents in the veins 630 or the arteries 640 may interfere with the electric signal that was transmitted into the veins or artery layer because the blood constituents may absorb a portion of the electric signal, create noise within the electric current, or absorb all of the electric current. In one example, for every three millimeters that the impedance pads are separated, the depth of tissue that the electric signal reaches increases by 1 millimeter.

In another example, the electronic device 600 may detect an electric signal that has passed through the vascular system at the wrist. In this example, the impedance pads 650 and 660 of the electronic device 600 may be separated by a fixed distance between 20 mm and 30 mm to measure a portion of the electric signal that has passed through the vascular system of the wrist. In another embodiment, if the electronic device 600 is measuring an electric signal that has passed through interstitial fluid of a superficial vascular area of the body, such as the fingertip, the impedance pads may be separated by a fixed distance of between 7 mm to 12 mm. In another example, if the measurement is being taken at an area of the body that is more muscular than the wrist, such as the bicep or thigh, the impedance pads may be separated by a fixed distance of between 30 mm to 60 mm.

In another embodiment, the portion of the electric signal received by the second impedance pad 660 depends in part on the size of the impedance pads 650 and 660 and the power level of the electric signal transmitted from the first impedance pad 650. For instance, a second impedance pad 660 with a surface area of 5 mm$^2$ may receive a larger portion of the electric current transmitted by the first impedance pad 650 than when the second impedance pad 660 has a surface area of 3 mm$^2$. In one embodiment, the size and spacing of the impedance pads may be different depending on the part of the body where the measurement is taking place. In one example, when an impedance measurement is being taken at the wrist, a shallow measurement may be taken to avoid veins and arteries that are close to the surface of the skin. In this example, the fixed distance may be spaced closer together when measuring at the wrist location than the fixed distance would be when measuring at the arm to take a shallow measurement. In a second example, the impedance pads may have less surface area to take a measurement at a location, such as the wrist, where a more shallow measurement would provide a more accurate measurement. In another example, when an impedance measurement is being taken at the arm, a deeper measurement may be taken because the veins 630 and arteries 640 are located further below the surface of the skin. In this example, impedance pads 650, 660 may have more surface area and/or the fixed distance may be larger.

In one embodiment, to prevent a portion of the electric signal that has been transmitted from the first impedance pad 650 but that has not entered the body from reaching the second impedance pad 660 and biasing a measurement, a non-conductive material may be placed between the first impedance pad 650 and the second impedance pad 660. In one example, the non-conductive material can be glass, porcelain, plastic, or rubber.

Figure 7:
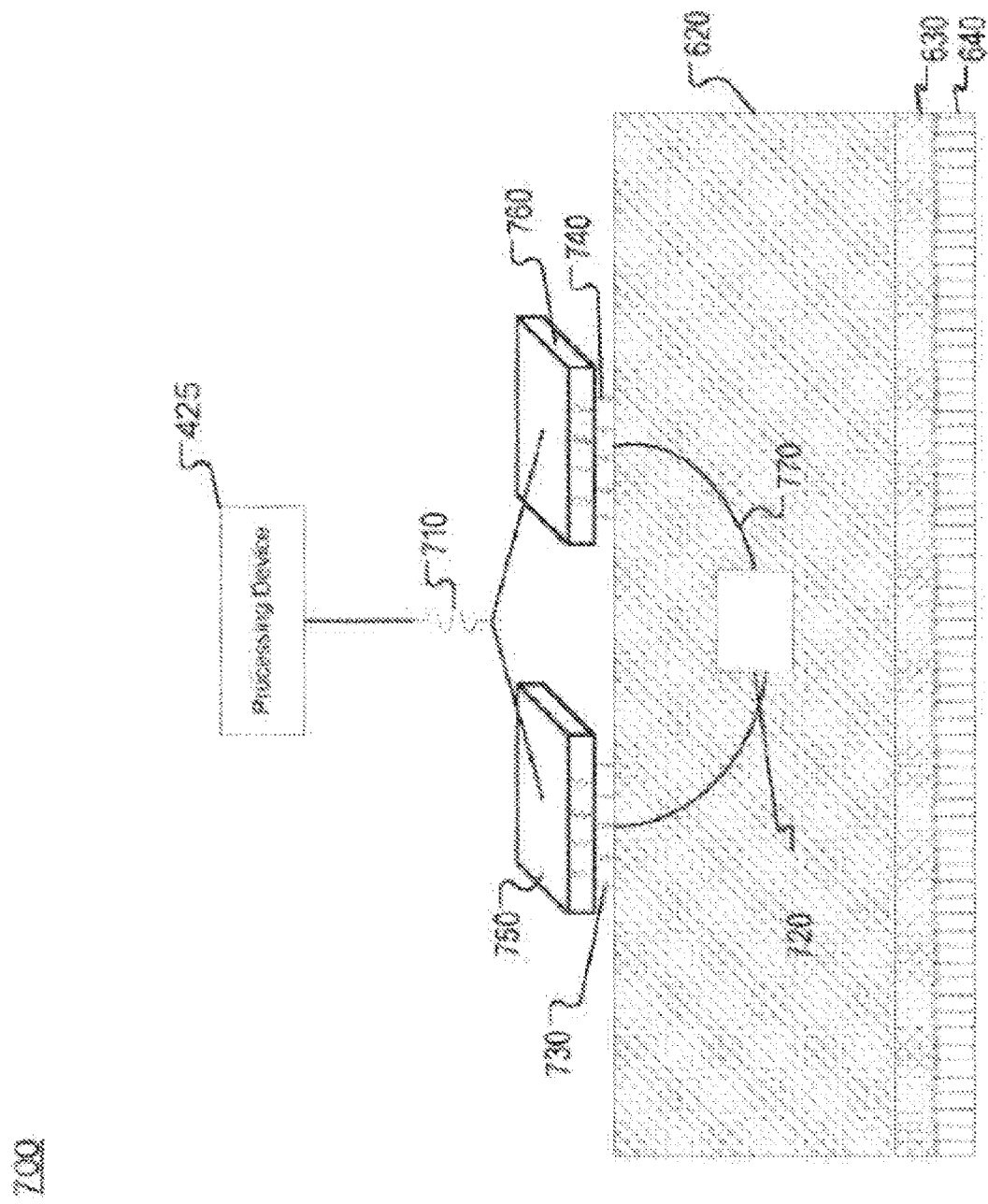
FIG. 7 depicts a processing device taking an impedance measurement from the body of a user.

FIG. 7 illustrates a processing device 425 (FIG. 4) taking an impedance measurement 720 from the body of a user, according to one embodiment. In one embodiment, impedance sensor may transmit electric signal 770 from a first impedance pad 750 into the skin of a user. The human skin includes an epidermis layer, a dermis layer 620 (FIG. 6), and a subcutaneous fat layer. Below the skin are veins 630 and arteries 640 (FIG. 6). In one embodiment, an electric signal may be transmitted into the dermis or epidermis layer of the skin. An impedance measurement 720 may be taken from the dermis layer 620 (FIG. 6) or epidermis layer because these layers develop sweat when a body perspires.

The impedance measurement may be effected by one or more resistances or impedances in the measurement process. In one embodiment, air resistance 730 and 740 may interrupt the impedance measurement 720 performed by the electronic device 700. In one example, sweat, electrocardiogram gel, water, spit, or other conductive solution may be used to minimize any airgaps between the surface of the skin and the impedance pads 750 and 760. In one embodiment, first impedance pad 750 and second impedance pad 760 are recessed into the housing to reduce or minimize the air resistance 730 and 740 between the impedance pads 750 and 760 and the skin. Further, the impedance pads 750 and 760 may be constructed out of a conductive material with a resistance quality of equal to or less than 10 mega ohms to minimize the resistance in the impedance pads themselves.

In one embodiment, impedance that is inherent in the electronic device 700 may be controlled so that a change in the impedance detected in the body may be determined. In one example, impedance may be detected by the electronic device 700 as a result of air resistances 730 and 740. Further, in this example, impedance may be detected by the electronic device 700 as a result of corrosion of the impedance pads 750 and 760. Further, in this example, impedance may be detected by the electronic device 700 due to dirt or other debris accumulating in the pores of impedance pads 750 and 760. By controlling these inherent impedances, the electronic device 700 can compensate for the controlled inherent impedances and detect a change in impedance in the body.

In one example, contact impedance is controlled by increasing the conductivity between the impedance pads 750 and 760 and the body. Contact impedance is impedance measured by the electronic device 700 as a result of air resistances 730 and 740. Contact impedance may be minimized by improving the conductivity between the impedance pads 750 and 760 and the skin through use of sweat, electrocardiogram gel, water, spit, or another conductive solution. In one example, electrocardiogram gel is used to minimize contact impedance to a negligible value between impedance pad 750 or 760 and the skin. In this example, the contact impedance may be stabilized between one or more impedance measurements to determine a hydration condition of a user. In this example, if a measurement is taken at the wrist with negligible contact impedance, using the electronic device 700 as described in proceeding paragraphs, the electronic device 700 may detect impedance in the body of less than 1,000 ohms. In another example, if the contact impedance is not negligible due to corrosion in the contact pads or air resistance between the impedance pads 750 and 760 and the skin, the electronic device 700 may detect impedance of up to 20,000 ohms in the skin.

In another example, if the same measurement were taken at an area of the body having a composition of fat, muscle, veins, and arteries different from the wrist, the electronic device 700 may detect an impedance measurement outside of the foregoing range. In another example, the separation of the impedance pads 750 and 760 may affect the impedance because the volume of body composition being measured increases as the separation of impedance pads 750 and 760 increases. In one example, the impedance level between the impedance pads 750 and 760, that is detected by the electronic device 700, will decrease when a distance between the impedance pads 750 and 760 decreases. In this example, the impedance level will decrease because the electronic signal goes through less body composition as the distance between the impedance pads 750 and 760 decreases. In one example, the impedance measurement is measured in ohms per millimeter. In another example, as the distance being measured increases the impedance detected will increase because the electric signal is traveling through more body mass. In another example, the electronic device is performing a localized measurement. In other words, the measurement is being determined at the wrist, fingertip, thigh, etc.

Figure 8:
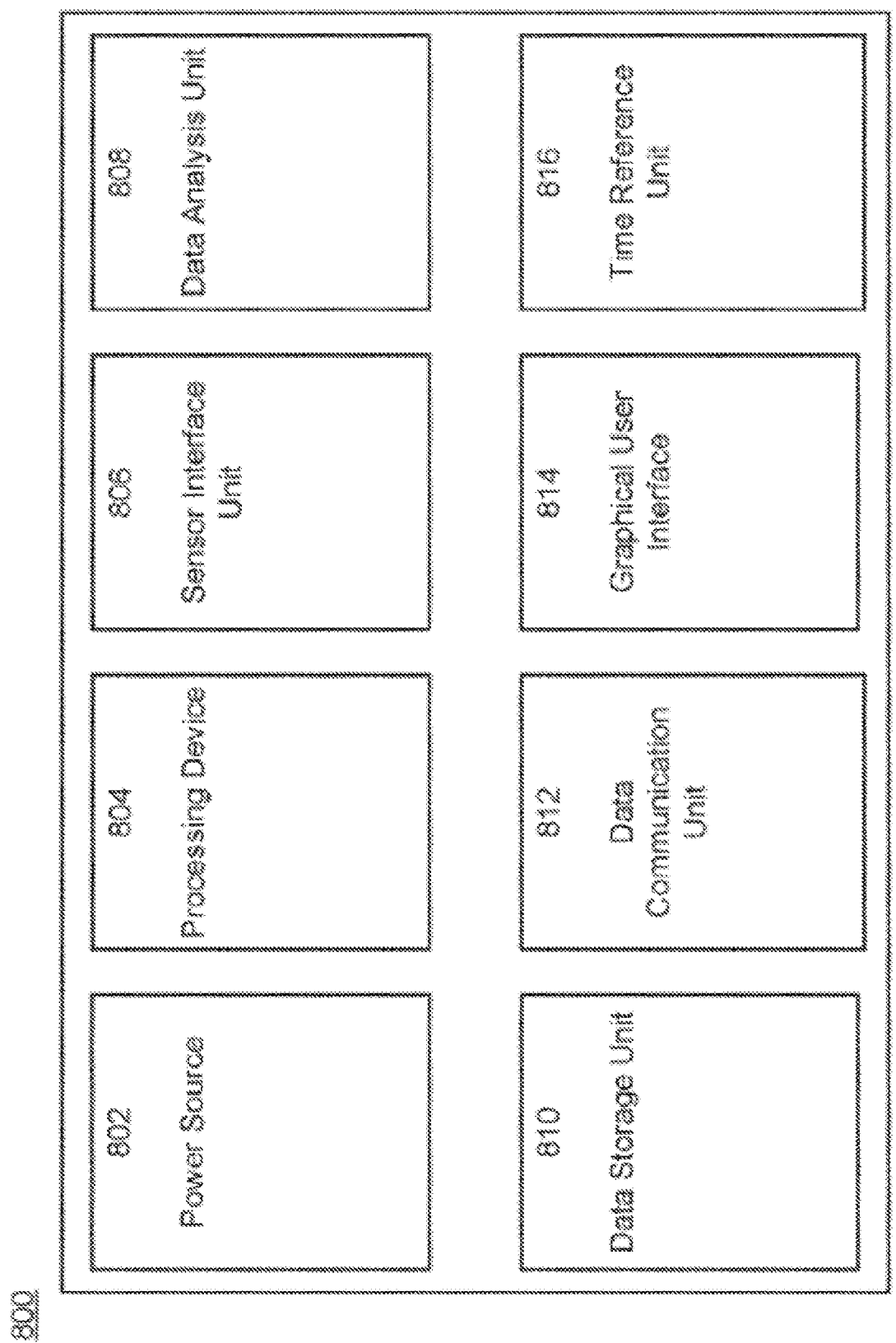
FIG. 8 depicts a block diagram of the electronic device, according to one embodiment.

FIG. 8 illustrates a block diagram of the electronic device 800, according to one embodiment. The electronic device 800 may include a power source 802, a processing device 804, a sensor interface unit 806, an analysis unit 808, a data storage unit 810, a data communication unit 812, a graphical user interface 814, and a time reference unit 816.

In one embodiment, the electronic device 800 includes a power unit 802 that supplies power to components of the electronic, device 800. The power unit 802 may include a battery to supply power and a charging unit that charges the battery. Alternatively, electronic device 800 is connectable to an energy source that powers the electronic device 800. In one embodiment, a charger may be used to recharge a battery or other energy source of the power unit 802.

In another embodiment, the electronic device 800 includes a processing device 804. The processing device 804 may include a central processor to process the data and/or information of the other components that make up the electronic device 800 or other units, interfaces, and/or devices attached to or in communication with the electronic device 800.

In another embodiment, the electronic device 800 may include a sensor interface unit 806. The sensor interface unit 806 may be coupled to one or more sensors, such as the optical sensor, the impedance sensor, or the humidity and/or temperature sensor, and may perform one or more measurements relating to a physiological condition of a body using the one or more of the sensors. In another embodiment, the sensor interface 806 may be coupled to the processing device 804. The sensor interface 806 can use the one or more sensors to take measurements relating to a hydration condition of a body, an impedance measurement, a temperature of a body or of an environment, a humidity measurement of a body or of an environment, or another physiological state or environment condition. In one example, the sensor interface 806 may be coupled to the processing device 804 and the optical sensor. In this example, the sensor interface unit 806 may receive data from the optical sensor relating to a portion of light that was reflected off an artery or other muscular-walled tube. Alternatively, the sensor interface 806 and the processing device 804 may be the same component. The sensor interface unit 806 may measure the backscatter of one or more wavelengths that have been reflected off a vein, artery, or other muscular-walled tube using the portion of light.

In one embodiment, the electronic device 800 may include a time reference unit 816 that generates time reference data usable to control the time at which data is collected from the sensor interface unit 806. The time reference unit 816 may also be used to calculate spatial and/or temporal derivatives between information received from the sensor interface unit 806. In one embodiment of the disclosure, the time reference unit 816 may keep track of the calendar time, such as a clock. Alternatively, the time reference unit 816 may act as a timer, keeping track of a lapsed time or decrementing from a defined time to zero. The timer of the time reference unit 816 may be used to collect information or data from the sensor interface 806 for a defined period of time or to record how long the sensor interface 806 collects data.

In one embodiment, the electronic device 800 includes a data analysis unit 808. The data analysis unit 808 may be communicatively coupled to the processing device 804, sensor interface unit 806, time reference unit 816, and other components of the electronic device 800. The data analysis unit 808 may determine that a hydration condition has changed for a user by comparing temporal data from the time reference unit 816 to measurement data from the sensor interface unit 806. The data analysis unit 808 may communicate the hydration condition to a user through the graphical user interface (GUI) 814.

In one embodiment, the electronic device 800 includes a graphical user interface 814. The graphical user interface may be a monitor screen, liquid crystal display (LCD), LED display, or the like. In aspect, the GUI may present information such as a hydration condition to the user. In another aspect, the user may be able to interact with the electronic device though inputs or icons on the GUI.

Figure 9A:
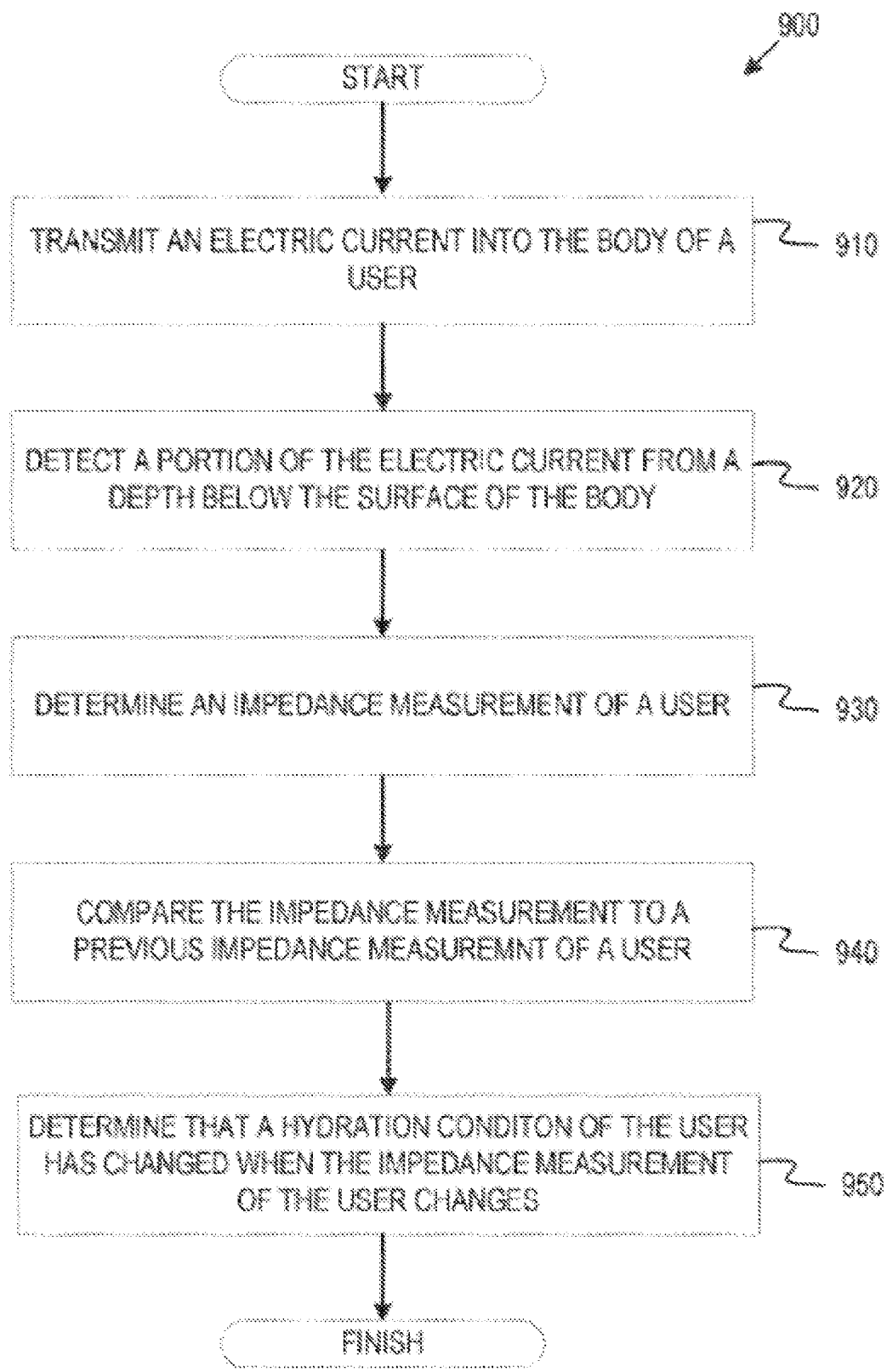
FIG. 9A depicts a flow diagram of a method of determining a hydration condition, according to one embodiment.

FIG. 9A illustrates a flow diagram of a method 900 of determining a hydration condition, according to one embodiment. The method 900 may be performed by processing logic that may include hardware (e.g., circuitry, dedicated logic, programmable logic, microcode, etc.), software (such as instruction run on a processing device, a general purpose computer system, or a dedicated machine, firmware, or a combination thereof. In one embodiment, the method 900 may be performed, in part, by processing logic of processing device 804.

For simplicity of explanation, the method 900 is depicted and described as a series of acts. However, acts in accordance with this disclosure can occur in various orders and/or concurrently and with other acts not presented as described herein. Furthermore, not all illustrated acts may be performed to implement the method 900 in accordance with the disclosed subject matter. In addition, those skilled in the art will understand and appreciate that the method 900 could alternatively be represented as a series of interrelated states via a state diagram or events.

The method can include the sensor interface using the first contact terminal of an impedance sensor to transmit an electric current into the body of a user (910). In one embodiment, the first contact terminal may be an electrode pad. The first contact terminal may be coupled to the sensor interface and the processing device.

The method can include, the sensor interface using the second contact terminal of the impedance sensor to receive a portion of the electric current from a depth below the surface of the body of the user (920). In one embodiment, the second contact terminal is separated from the first contact terminal by a fixed distance. In one example of this embodiment, the first and second contact terminals are separated by a fixed distance of 12 mm to 18 mm to measure the portion of the electric current that has traveled through the dermis or epidermis layer of the skin. Alternatively, for areas of the body where the veins and arteries are near the surface of skin, the fixed distance may be less than 12 millimeters. Moreover, in areas of the body where the veins and arteries are further below the surface of the skin, the fixed distance may be greater than 18 millimeters as was discussed in the preceding paragraphs. In another embodiment, the size of the contact terminals and the strength of the electric signal may affect the fixed distance that would be used to measure the portion of the electric signal that has traveled through the dermis or epidermis layer of the skin.

The method may include the processing device or sensor interface determining an impedance measurement of a user (930). The processing device or sensor interface may use the received portion of the electric signal from the optical sensor to perform the impedance measurement. The impedance measurement will be based at least in part on the strength of the received portion of the electric current or the speed at which the received electric current travels between the first contact terminal and the second contact terminal.

The method may further include the processing device or sensor interface comparing the impedance measurement to a previous impedance measurement (940). By comparing the impedance measurement to a previous impedance measurement, the processing device can determine if the impedance in the skin has increased or decreased. An increase in skin impedance may indicate that the skin is becoming dry. A decrease in skin impedance may indicate that the skin is perspiring or is otherwise becoming wet.

The method may further include the processing device or sensor interface determining that a hydration condition of the user has changed when the impedance measurement of the user changes (950). In one example, the processing device or sensor interface may determine that a person is becoming more hydrated when the impedance measurement of the skin has decreased from a normal skin impedance level of the user. In another example, the processing device or sensor interface may determine that a person is becoming less hydrated when the impedance measuring of the skin has increased from the normal skin impedance level of the user.

Figure 9B:
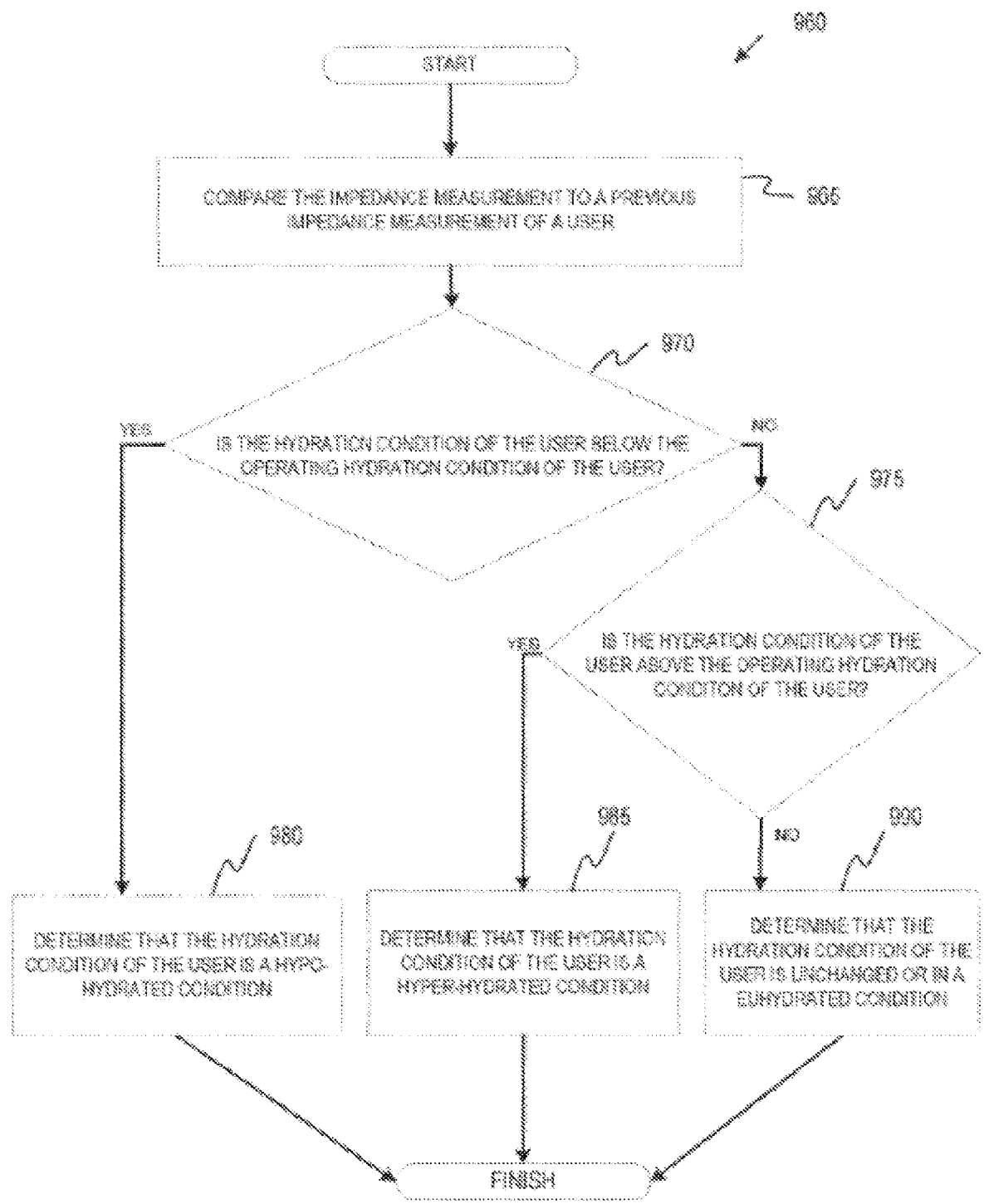
FIG. 9B illustrates a flow diagram of a method of determining a change in hydration condition of a user, according to one embodiment.

FIG. 9B illustrates a flow diagram of a method of determining a change in hydration condition of a user, according to one embodiment. The method 960 may be performed by processing logic that may include hardware (e.g., circuitry, dedicated logic, programmable logic, microcode, etc.), software (such as instruction run on a processing device, a general purpose computer system, or a dedicated machine, firmware, or a combination thereof. In one embodiment, the method 960 may be performed, in part, by processing logic of processing device 804.

For simplicity of explanation, the method 960 is depicted and described as a series of acts. However, acts in accordance with this disclosure can occur in various orders and/or concurrently and with other acts not presented as described herein. Furthermore, not all illustrated acts may be performed to implement the method 960 in accordance with the disclosed subject matter. In addition, those skilled in the art will understand and appreciate that the method 960 could alternatively be represented as a series of interrelated states via a state diagram or events.

The method begins by comparing an impedance measurement to a previous impedance measurement of a user determine a hydration condition of a user (965). A hydration condition of the user can include a dehydrated (hypo-hydrated), normal hydration level (euhydrated), or over-hydrated (hyper-hydrated) conditions. The impedance measurement can be determined by the sensor interface as discussed in the preceding paragraphs.

The method includes, determining, by the processing device, when the hydration condition of the user is below the operating hydration condition of the user by comparing the impedance measurement to the operating hydration condition of the user (970). In one embodiment, the operating hydration condition of the user can be determined by taking multiple measurements over a period of time and determining a range in which the user is within the user's operating hydration condition (e.g., euhydration condition).

In one embodiment, when the impedance measurement is above the operating hydration condition, the processing device or sensor interface may determine that the user is in dehydrated (hypo-hydrated) condition (980). If the impedance measurement is not below the operating hydration condition of the user, the processor may determine that the user is not in a hypo-hydrated condition. The processor may determine when the hydration condition of the user is above the operating hydration condition of the user (975). If the impedance measurement is above the normal operating hydration condition of the user; it may be an indicator that the user is in an over-hydrated (hyper-hydrated) condition (985). Alternatively, if the processing device or sensor interface determines that the user is neither above nor below the operating hydration condition of the user, that the user is maintaining their operating hydration condition and that the user is in a healthy hydration (euhydrated) condition (990).

Figure 10:
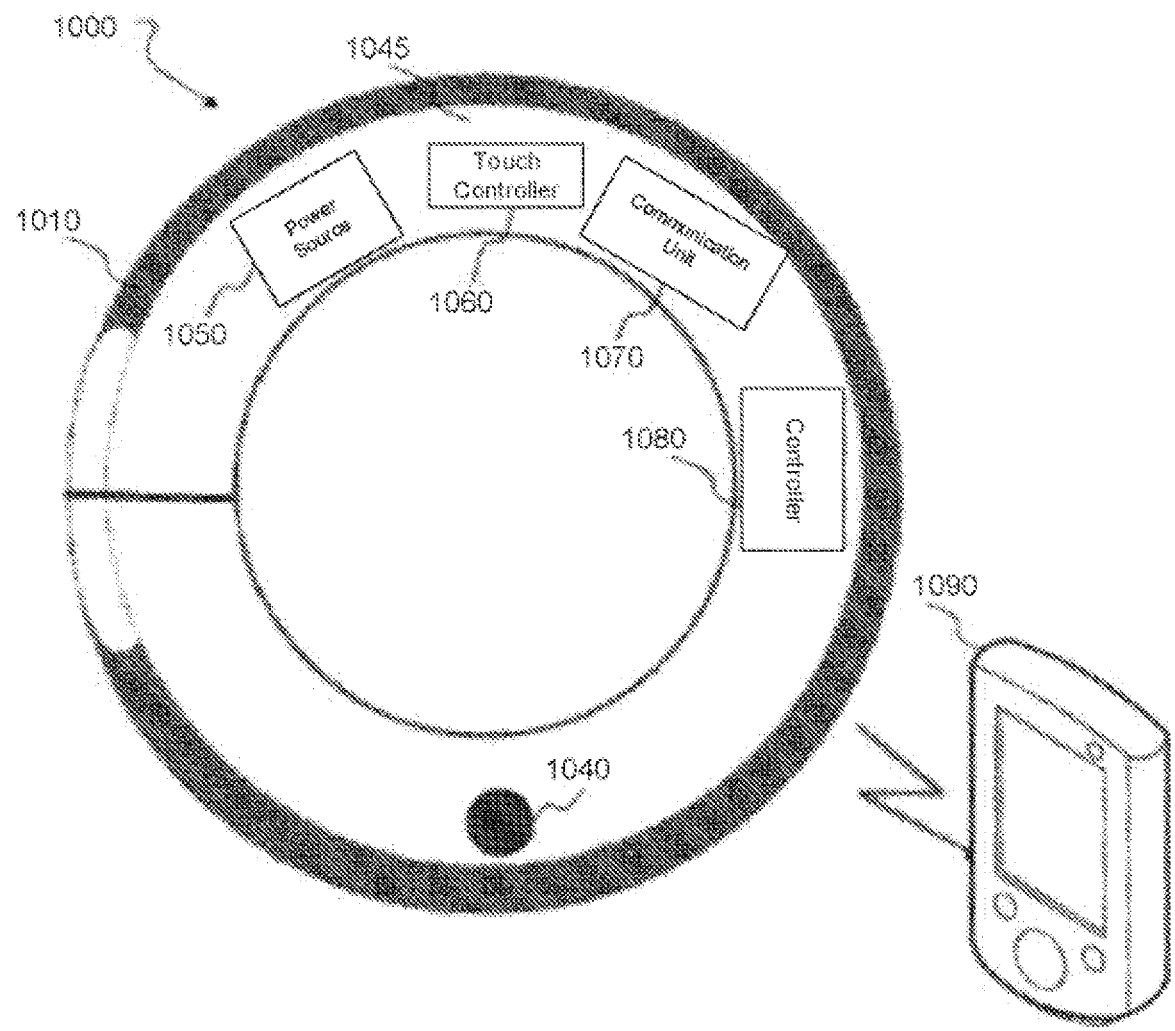
FIG. 10 depicts an electronic device communicating with an external electronic device, according to one embodiment.

Referring to FIG. 10, an electronic device 1000 communicating with an external electronic device 1090 is depicted, according to one embodiment. The electronic device 1000 can be a substantially circular band with an outer surface 1010 and an inner surface 1020. In one example, the outer surface 1010 or the inner surface 1020 can be made of flexible or non-rigid material, such as rubber, polyurethane, and so forth. In another example, the outer surface 1010 or the inner surface 1020 can be made of semi-rigid or rigid material, such as plastic, metal, and so forth. In another example, a portion of the outer surface 1010 or the inner surface 1020 can be the flexible or non-rigid material and a portion of the outer surface 1010 or the inner surface 1020 can be the semi-rigid or rigid material. In another example, a portion of the inner surface 1020 that contacts a body of the user is a conductive material. For example, one or more sensors 1040 are bio-impedance sensors that are conductive rubber pads that contact the body of the user and are used by processing logic to make bio-impedance measurements.

In one example, a cavity or chamber 1045 can be between the outer surface 1010 and an inner surface 1020. The cavity or chamber 1045 can include modules, units, systems, subsystems, or devices of the electronic device 1000. For example, the cavity or chamber 1045 can house a power source 1050, a graphical user interface or touch controller 1060, a communication unit 1070, a controller 1080, one or more sensors 1040, and/or other units. In one example, the communication unit 1070 can wirelessly communicate with an external electronic device 1090. In another example, the power source 1050 can provide power to other units or modules of the electronic device 1000. In one example the touch controller 1060 can receive user input from an input device. In one example, the input device can be a graphical user interface (GUI) or a touch display and be operable to receive input via the GUI or the touch display. In another example, the input device can receive communications from other devices via a communication network (e.g., a wireless network) or a communication connection (such as a universal serial bus). In another example, the controller 1060 can control systems and subsystems of the electronic device 1000.

In another example, the power source 1050 can be a battery, such as a rechargeable battery. The power source 1050 can receive power from another power source such as via a cord plugged into a power source or using wireless power such as inductive wireless charging or resonant wireless charging. In another example, the electronic device 1000 can have one or multiple sensors 1040 (e.g., a sensor array). In one example, the multiple sensors 1040 can be different types of sensors.

In one example, the electronic device 1000 can receive physiological information such as a hydration condition and/or an environmental condition of a user of the electronic device 1000 from another device. In another example, the electronic device 1000 can have a touch controller 1060 to receive user input physiological information and/or environmental information. In one example, a power source 1050, a touch controller 1060, a communication unit 1070, a controller 1080, one or more sensors 1040 can be in direct or indirect communication with each other. For example, the touch controller 1060 receives user input information from the input device and communicates the user input information to the controller 1080. In this example, the controller 1080 can include a processor or processing device to analyze or process the user input information. In another example, the sensor 1040 can take a physiological measurement and communicate physiological information to the external electronic device 1090 via the communication unit 1070. In one embodiment, the external electronic device 1090 is an electronic device with a processor, such as a smartphone, electronic tablet, or personal computer. In another embodiment, the external electronic device 1090 is a cloud computing system or a server. The external electronic device 1090 can analyze or process data or information received from the electronic device 1000. In one example, the external electronic device 1090 can store the processed data or information. In another example, the external electronic device 1090 can send the processed data or information back to the electronic device 1000.

Figure 11:
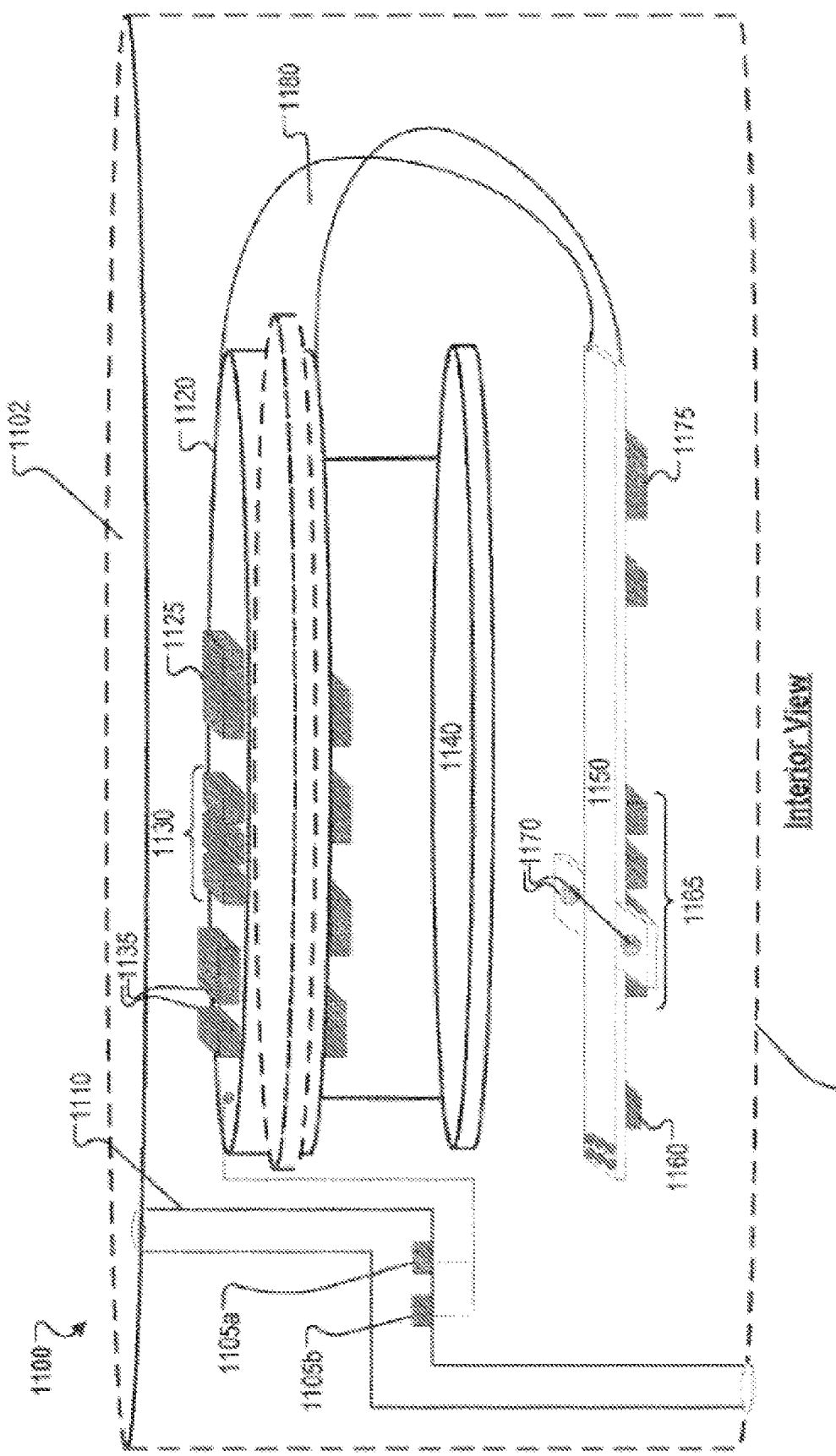
FIG. 11 depicts an interior view of the electronic device, according to one embodiment.

FIG. 11 illustrates an interior view of the electronic device 1100, according to one embodiment. The electronic device 1100 may include a bottom side 1101 and a top side 1102. In one embodiment, the electronic device 1100 may have a flume extending from the bottom side 1101 to the top side 1102. The flume may allow humidity and/or temperature sensors 1105 to detect the humidity and temperature of both the air and the skin of the user.

In one embodiment, the electronic device 1100 may include a flexible circuit board 1180 with an upper section 1120 and a lower section 1150. The upper section 1120 of the flexible circuit board 1180 may include a motion processing unit (MPU) 1125, display LEDs or a graphical user interface 1130, and one or more communication components 1135 such as a Bluetooth Low Energy component. In one embodiment, the MPU may detect movement of electronic device and relay motion information to the sensor interface unit 806. Additionally, display LEDs or GUI 1130 may be used to inform the user of a hydration condition. The lower section 1150 of the electronic device 1100 may include a thermistor 1175, optical components 1165, impedance sensor contact terminals 1170, and a vibrator 1160. In one embodiment, the vibrator 1160 may be utilized to inform the user when a hydration condition has changed or to provide additional relevant information to the user.

Figure 12:
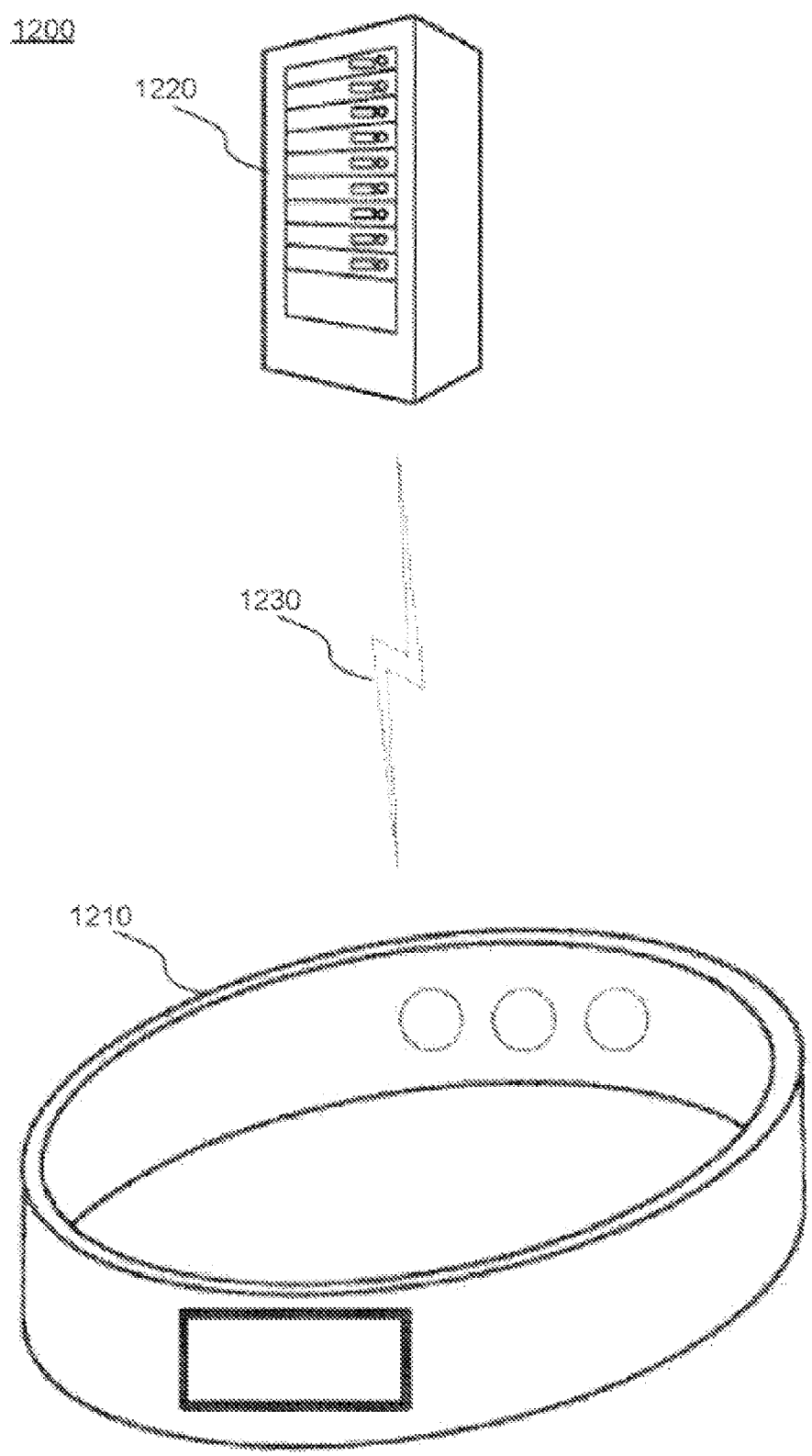
FIG. 12 depicts an electronic device in direct communications with a computing device, according to one embodiment.

FIG. 12 illustrates an electronic device 1200 in direct communications with a computing device 1220, according to one embodiment. In one example, sensor measurements collected and/or stored by the electronic device 1210 can be processed or analyzed by a processor or processing device of the electronic device 1200 and/or by a computing device 1220 in communication with the electronic device 1200. The electronic device 1200 can be indirect communication 1230 with the computing device 1220. In one example, the direct communication 1230 can be a Bluetooth® communication link, a Zigbee® communication link, radio signal, or other direct communication systems. In another example, the other computing device 1220 can be a server that stores information, such as sensor measurements or hydration condition information previously taken by the electronic device 1210 or sensor measurements or hydration condition information taken from a group of individuals, as discussed herein. In another example, the computing device 1220 can be a mobile computer device, such as a laptop computer, tablet, or a smartphone. The electronic device 1200 can communicate information, such as sensor measurements or hydration condition information, to the computing device 1220. In one example, the computing device 1220 can process and/or analyze the sensor measurements and/or information received from the electronic device 1200. In another example, the computing device 1220 can send processed data, analyzed data, measurement results, and/or other information to the electronic device 1200. In another example, the computing device 1220 can communicate calibration information to the electronic device 1210.

Figure 13:
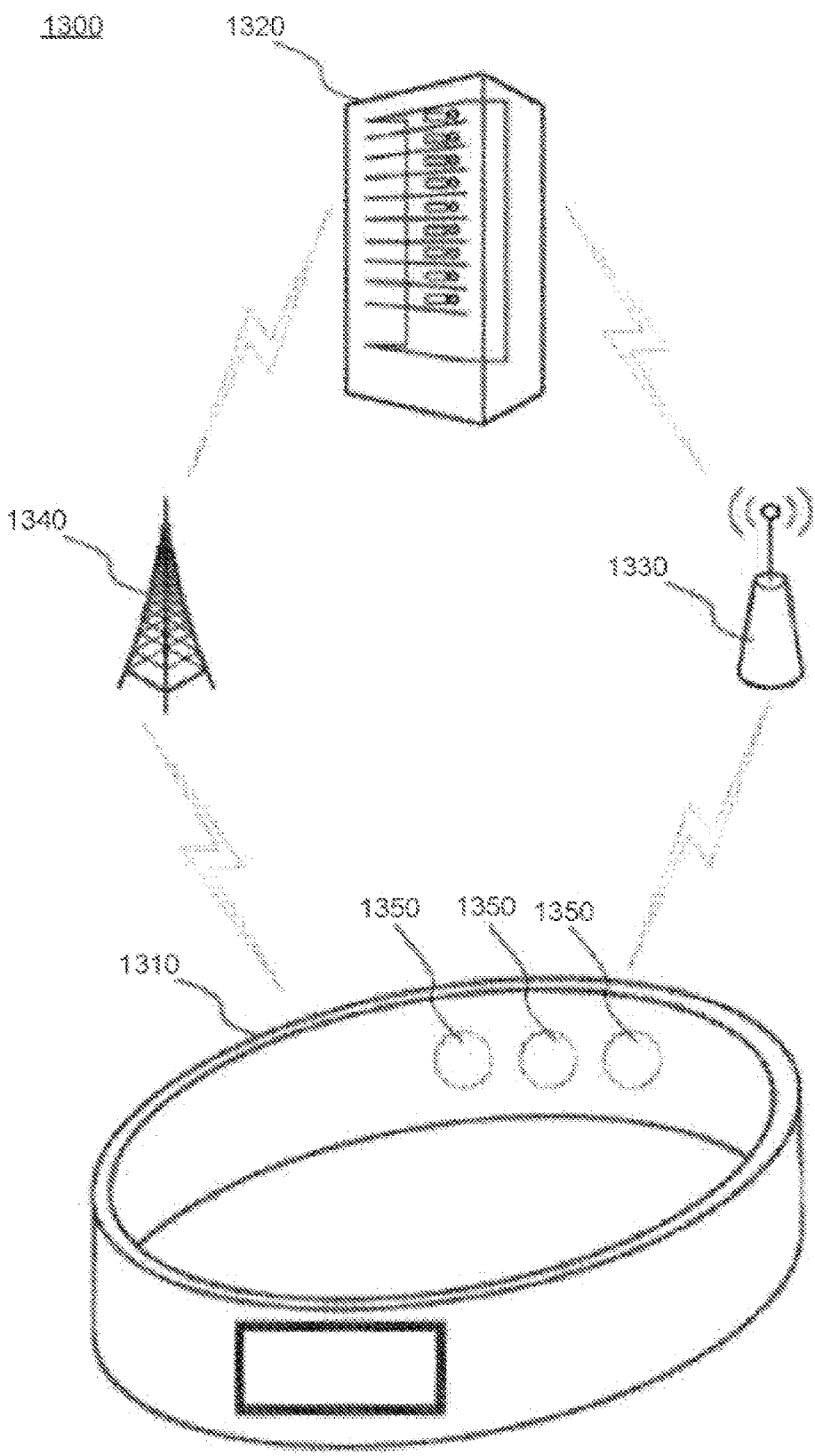
FIG. 13 depicts an electronic device and a computing device in indirect communication using a communications network, according to one embodiment.

FIG. 13 illustrates an electronic device 1300 and a computing device 1320 in indirect communication using a communications network according to one embodiment. In one embodiment, the electronic device 1300 can be a standalone device with a processing device to analyze or process: information taken from one or more sensors 1350 of the electronic device 1300; information received from other devices; and/or information stored in a memory of the electronic device 1300.

In another embodiment, the electronic device 1300 communicates locally with the computing device 1320 use a wireless communication network 1330 or a cellular communication network 1340. The local computing device 1320 can be a smartphone, tablet device, personal computer, laptop, a local server, and so forth. In another embodiment, the electronic device 1300 communicates with a non-local or remote computing device 1320 using a wireless communication network 1330 or acellular communication network 1340. The non-local or remote computing device 1320 can be a remote server, a cloud-based server, a back-end server, or other remote electronic devices.

In one example, the wireless communication network 1330 is a cellular network employing a third generation partnership project (3GPP) release 8, 9, 10, 11, or 12 or Institute of Electronics and Electric Engineers (IEEE) 802.16p, 802.16n, 802.16m-2011, 802.16h-2010, 802.16j-2009, 802.16-2009. In another example, the electronic device 1300 may provide a secure wireless area network (WLAN), secure PAN, or wireless fidelity (Wi-Fi) Private Wireless Wide Area Network (PWAN) to communicate with the computing device 1320. The electronic device 1300 in the WLAN may use the Wi-Fi® technology and IEEE 802.11 standards defined by the Wi-Fi Alliance® such as the IEEE 802.11-2012, IEEE 802.11ac, or IEEE 802.11ad standards. Alternatively, the electronic device 1300 and the computing device 1320 in the WLAN may use other technologies and standards. Similarly, the electronic device 1310 in the PAN or WPAN may use a Bluetooth® technology and IEEE 802.15 standards defined by the Bluetooth Special Interest Group, such as Bluetooth v1.0, Bluetooth v2.0, Bluetooth v3.0, or Bluetooth v4.0 (including Bluetooth low energy). Alternatively, the electronic device 1300 in the secure PAN may use other technologies and standards. In another embodiment, the communications network may be a Zigbee® connection developed by the ZigBee Alliance such as IEEE 802.15.4-2003 (Zigbee 2003), IEEE 802.15.4-2006 (Zigbee 2006), IEEE 802.15.4-2007 (Zigbee Pro). The WAN or PWAN can be used to transmit data over long distances and between different LANs, WLANs, metropolitan area networks (MANs), or other localized computer networking architectures.

The electronic device 1300 and the computing device 1320 can be in indirect communication using a communications network such as wireless communication network 1330 (such as a Wi-Fi® network) and/or using acellular communication network 1340 (such as a 3rd Generation Partnership Project (3GPP® network) to communicate data or measurement information. In one example, the electronic device 1300 can take sensor measurements using a sensor 1350 and communicate the sensor measurements to the computing device 1320 via the wireless communication network 1330 and/or the cellular communication network 1340. In another example, the computing device 1320 can receive sensor measurements from the electronic device 1300 via the wireless communication network 1330 and/or the cellular communication network 1340 and process the sensor measurements and/or analyze the sensor measurements. When the computing device 1320 has processed the sensor measurements and/or analyzed the sensor measurements, the computing device 1320 can communicate the processed sensor measurements, analyzed sensor measurements, sensor measurement results, or other information to the electronic device 1300 via the wireless communication network 1330 and/or the cellular communication network 1340.

FIG. 14 depicts a body area network (BAN) devices 1462-1476 communicating using a BAN, according to one embodiment. In one embodiment, the BAN can include a wired body area network, a wireless body area network (WBAN), and/or a body sensor network (BSN). The BAN can include multiple wearable computing devices or wearable sensor devices 1462-1476 that are in communication with each other to send and receive data and information. In one example, the BAN devices can include: a BAN device 1460 that is attached or coupled to the body of the user; a BAN device 1462 that is implanted into the body of the user; a BAN device 1468 that is embedded into the body of a user; a BAN device 1470 that is mounted on a surface of the body, and so forth. In another example, the BAN devices can include devices adjacent the user including: a BAN device 1464 shaped to fit in a clothes pockets of the user, a BAN device 1466 that a user can carry, such as a handheld device; a BAN device 1472 that is integrated into clothes of the user; a BAN device 1476 located in a user's bag, a BAN device 1474 integrated into a user's bag, and so forth. In one embodiment, an electronic device is a BAN device. In another embodiment, the BAN devices 1462-1476 can be body sensor units (BSUs) that include a processing device, a sensor, and a communication device. The BSUs can communicate with a body central unit (BCU) 1478 that is a hub for the BAN devices. The BCU 1478 can be located at any of the locations discussed above for the BAN devices 1462-1476. The BCU 1478 can include a processing device, memory, a communication device, and a display. The BCU 1478 can receive data from a BAN device 1462-1576 and analyze the data. In one example, the BCU 1478 can display the analyzed data using the display of the BCU 1478. In another example, the BCU 1478 can send the analyzed data to a BAN device 1462-1476 or another device. One advantage of the BCU 1478 communicating with the BAN devices 1462-1478 is that the BAN devices 1462-1478 can be configured to be minimal sensor devices with low power consumption and a compact design where the BCU 1478 performs the processing of the data.

In another embodiment, the BCU 1478 can be a data hub or data gateway to manage the BAN devices 1462-1476. In another embodiment, the BCU 1478 can provide a user interface to control the BAN devices 1462-1476. In another embodiment, the BAN devices 1462-1476 and/or the BCU 1478 can use wireless private area networks (WPAN) technology as a gateway or relay to reach longer ranges. In one example, the BCU 1478 can us a WPAN to connect the BAN device 1462-1476 on the body to the internet. For example, medical professionals can access patient data from the BAN devices 1462-1476 online using the internet independent of a location of a patient.

Figure 15:
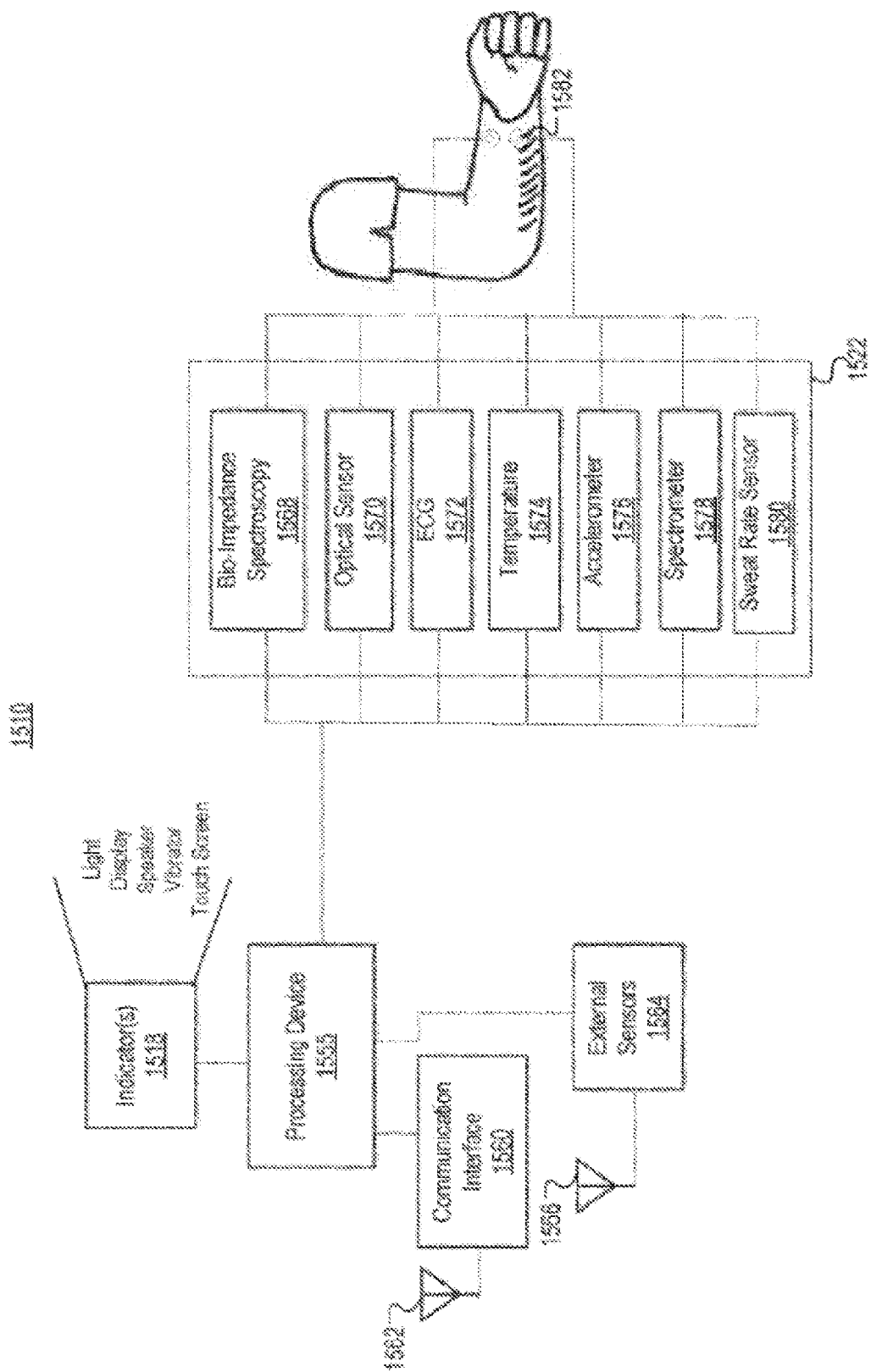
FIG. 15 depicts a schematic view of an electronic device, according to one embodiment

FIG. 15 depicts a schematic view of an electronic device 1510, according to one embodiment. The electronic device 1510 may include the indicators 1518, a sensor array 1522 (to include at least one of the sensors in FIG. 1, 2, 4, 5, or 7), a processing device 1555, a communications interface 1560, an antenna 1562 coupled with the communications interface 1560, external sensors 1564, and accompanying antenna(s) 1566. In one example, the sensor array 1522 may include one or more physiological sensors to take physiological measurements (e.g., measurements related to the body of the individual or animal). The sensor array 1522 may include one or more sensors to engage a user of the electronic device to take measurements. In various examples, the sensor array 1522 may include, without limitation: abio-impedance spectroscopy sensor 1568 (or simply impedance sensor 1568), an optical sensor 1570, an electrocardiogram (ECG) sensor 1572, a temperature sensor 1574 (such as a thermometer or thermistor), an accelerometer 1576, a spectrometer 1578, a sweat rate sensor 1580, and so forth. In one example, the sensor array 1522 can contact or engage the body of the user at allocation 1582.

Figure 16:
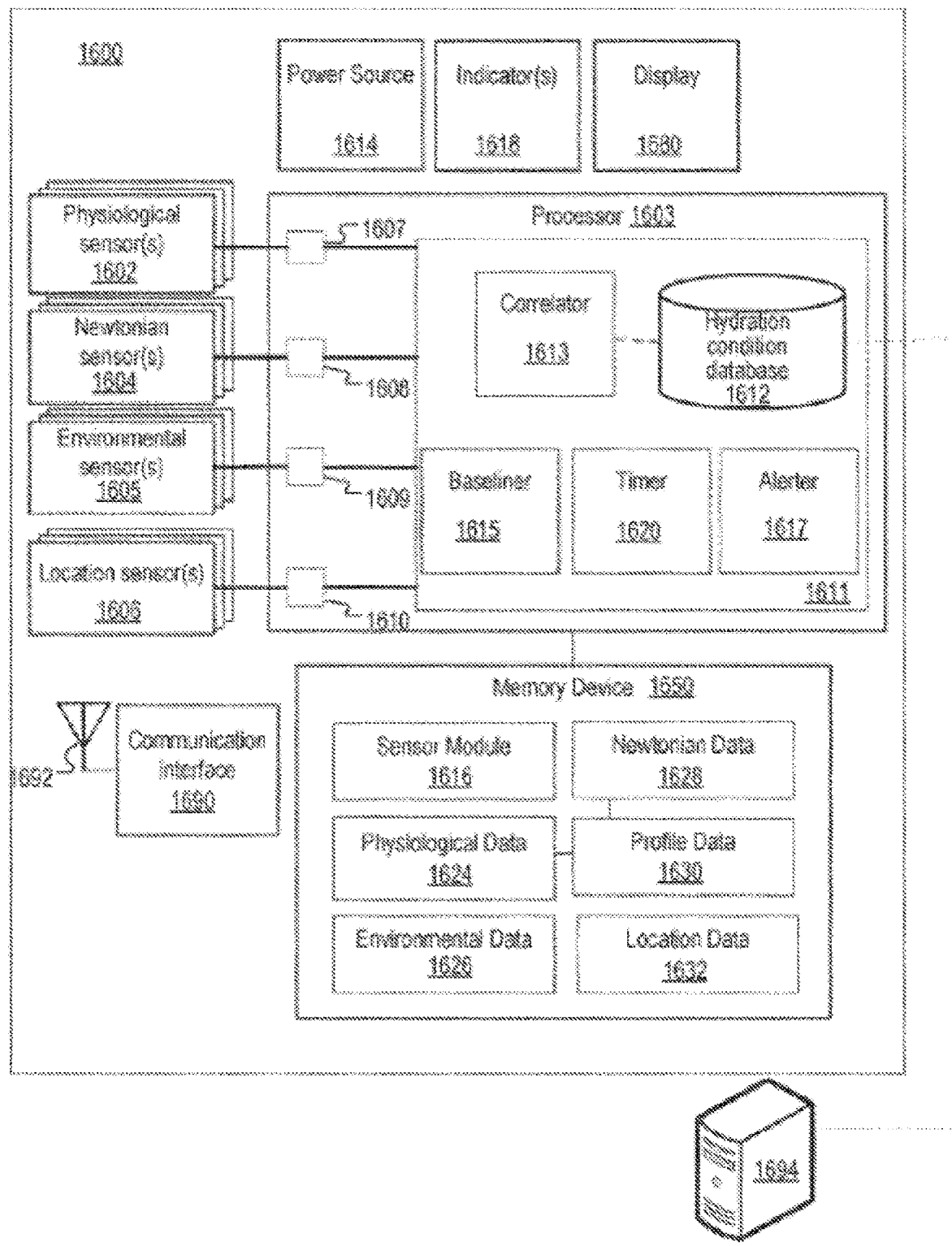
FIG. 16 is a block diagram of the electronic device with a correlator, a baseliner, and an alerter, according to one embodiment.
Figure 18:
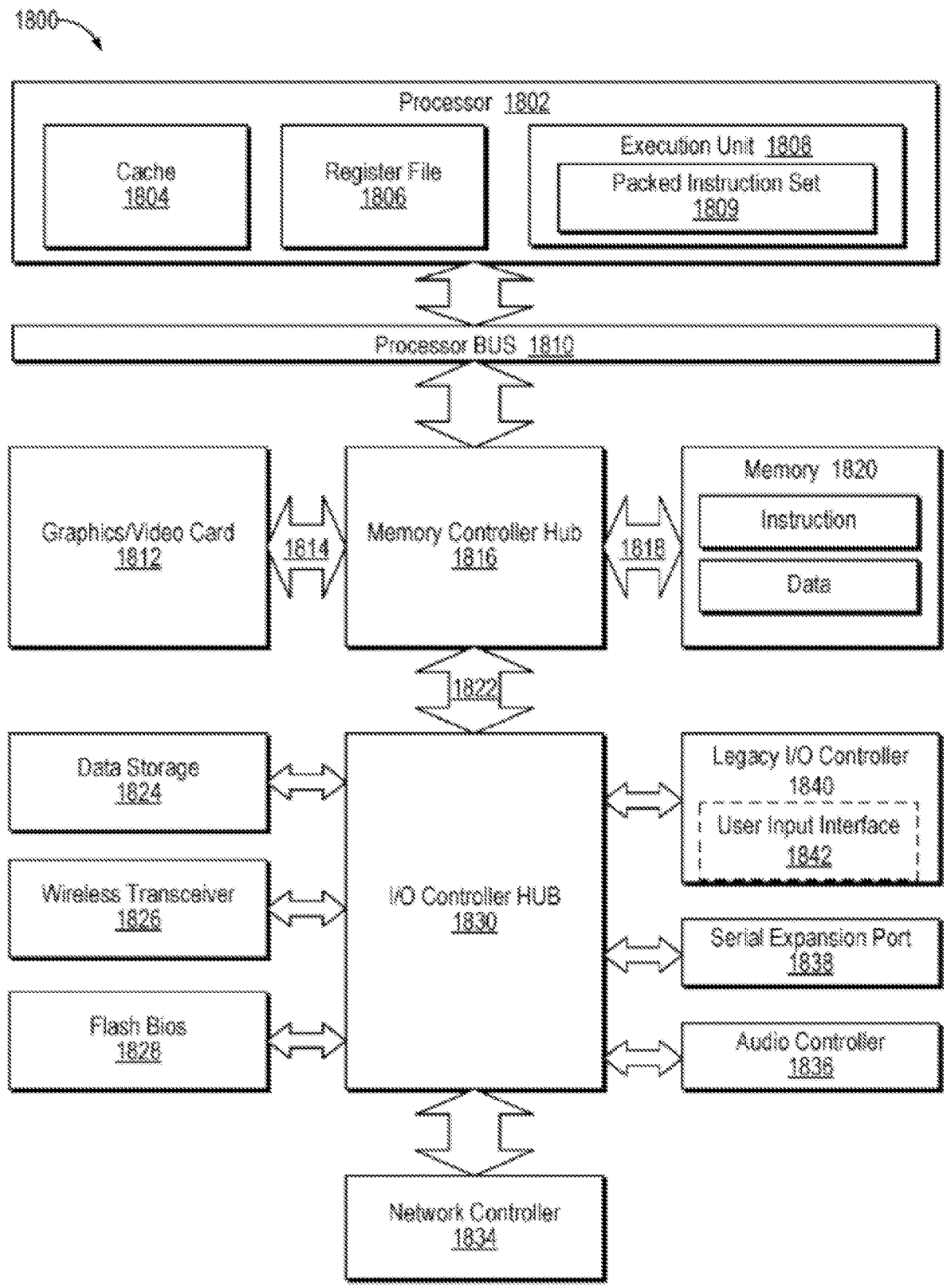
FIG. 18 a block diagram of an exemplary computer system formed with a processor that includes execution units to execute an instruction, where one or more of the interconnects implement one or more features in accordance with one example implementation of the present disclosure is illustrated.

FIG. 16 is a block diagram of the electronic device 1600 with a correlator 1613, a baseliner 1615, and an alerter 1617, according to one embodiment. The electronic device 1600 may include, without limitation, one or more physiological sensor(s) 1602, one or more Newtonian sensor(s) 1604, one or more environmental sensor(s) 1605, one or more location sensor(s) 1604, a processor 1603, a memory device 1650, a display 1680, a communication interface 1690 (such as a radio frequency (RF) circuit), and an antenna 1692 coupled to the communication interface 1690.

In one embodiment, the communication interface 1690 may communicate, via the antenna 1692, with an external electronic device 1090 (illustrated in FIG. 10), a computing device 1320 or 1420 (illustrated in FIGS. 13 and 14), and with other wireless devices such as electronic devices 1610 of other users. In one example, the communication interface 1690 may communicate the information using a cellular network, a wireless network, or a combination thereof. In one example, the communications network can be a cellular network employing a third generation partnership project (3GPP) release 8, 9, 10, 11, or 12 or Institute of Electronics and Electric Engineers (IEEE) 802.16p, 802.16n, 802.16m-2011, 802.16h-2010, 802.16j-2009, 802.16-2009. In another example, the electronic device 1600 may provide a secure wireless area network (WLAN), secure PAN, or wireless fidelity (Wi-Fi) Private Wireless Wide Area Network (PWAN) to communicate with a device. The electronic device 1600 in the WLAN may use the Wi-Fi® technology and IEEE 802.11 standards defined by the Wi-Fi Alliance® such as the IEEE 802.11-2012, IEEE 802.11ac, or IEEE 802.11ad standards. Alternatively, the devices in the WLAN may use other technologies and standards. Similarly, the electronic device 1600 in the PAN or WPAN may use the Bluetooth® technology and IEEE 802.15 standards defined by the Bluetooth Special Interest Group, such as Bluetooth v1.0, Bluetooth v2.0, Bluetooth v3.0, or Bluetooth v4.0. Alternatively, the electronic device 1600 in the secure PAN may use other technologies and standards. In another embodiment, the communications network may be a Zigbee® connection developed by the ZigBee Alliance such as IEEE 802.15.4-2003 (Zigbee 2003), IEEE 802.15.4-2006 (Zigbee 2006), IEEE 802.15.4-2007 (Zigbee Pro). The WAN or PWAN can be used to transmit data over long distances and between different LANs, WLANs, metropolitan area networks (MANs), or other localized computer networking architectures.

In one embodiment, the electronic device 1600 can communicate data with the other devices via another device, such as a smartphone or tablet computing device. For example, the communication interface 1690 can pair with a smartphone via the wireless network. The smartphone can receive data using the wireless network and can communicate the data to the other device. In another embodiment, the electronic device 1600 may communicate information with the other device via repeaters or a relay system. For example, a user of the electronic device 1600 can be outside a coverage area for the cellular network or the wireless network, e.g., a farm worker out in the field. In this example, the electronic device 1600 can determine that it is outside the coverage area and switch to communicating via the repeaters or the relay system.

In one embodiment, the electronic device 1600 can determine it is outside a coverage area when it does not receive a signal from the cellular network or the wireless network. In another embodiment, the electronic device 1600 can ping the cellular network or the wireless network (such as a tower within the cellular network or the wireless network) and determine that it is outside the coverage area when the electronic device 1600 does not receive a reply to the ping. In another embodiment, multiple electronic devices 1610 can communicate with each other to form a piconet. In this embodiment, a first electronic device can determine it is outside the coverage area and can scan for a second electronic device, where the second electronic device is in the coverage area or in communication with another electronic device in the coverage area. When the first wearable safety finds the second electronic device, the electronic device can communicate information to an end device or to the cellular network or the wireless network via the second electronic device.

The processor 1603 may include a first sensor interface 1607 for receiving sensor data from the physiological sensor(s) 1602, a second sensor interface 1608 for receiving sensor data from the Newtonian sensor(s) 1604, a third sensor interface 1609 for receiving sensor data from the environmental sensor(s) 1605, a fourth sensor interface 1610 for receiving sensor data from the location sensor(s) 1606, and a processing element 1611. The processing element 1611 in turn may include a correlator 1613, a baseliner 1615 and/or an alerter 1617. The memory device 1650 may also include, without limitation, a sensor module 1606, physiological data 1624, environmental data 1626, Newtonian data 1628, and profile data 1630, location data 1632.

The electronic device 1600 may include the sensor array 120 (FIG. 1) with two or more sensors. In the depicted embodiment, the electronic device 1600 may include one or more physiological sensors 1602, one or more Newtonian sensors 1604, one or more environmental sensors 1605, one or more location sensors 1606; or a combination thereof. In some instances, the Newtonian sensors 1604 may be physiological sensors. That is, in some embodiment, the activity level may be determined from one or more physiological measurements.

A physiological measurement may be any measurement related to a living body, such as a human's body or an animal's body. The physiological measurement is a measurement made to assess body functions. Physiological measurements may be simple, such as the measurement of body or skin temperature, or they may be more complicated, for example measuring how well the heart is functioning by taking an ECG (electrocardiograph), or determining a hydration condition of the body. Physiological measurements may also include motion and/or movement of the body. In some cases, these physiological measurements may be taken as an aggregate, e.g., as physiological data, with which to correlate to other physiological measurements, a physiological parameter, and/or an environmental parameter.

A parameter may be considered a measurable quantity (such as heart rate, temperature, altitude, and oxygen level, as just a few examples). When measurements of parameters are taken in the aggregate, the measurements may form data which may be analyzed and correlated to other data or parameters, to identify trends or to identify when meeting (or exceeding) certain thresholds that trigger alerts or other actions and the like.

The physiological sensors 1602 may include a pulse oximeter sensor, an electrocardiography (ECG) sensor, a fluid level sensor, an oxygen saturation sensor, a body core temperature sensor, a skin temperature sensor, a plethysmograph sensor, a respiration sensor, a breath rate sensor, a cardiac sensor (e.g., a blood pressure sensor, a heart rate sensor, a cardiac stress sensor, or the like), an impedance sensor (e.g., bio-impedance spectroscopy sensor), an optical sensor, a spectrographic sensor, an oxygen saturation sensor, or a sweat rate sensor. Alternatively, other types of sensors may be used to measure physiological measurements, including measurements to determine activity levels of a person wearing the electronic device.

The Newtonian sensors 1604 may be any of the physiological sensors described above, but in some cases, the Newtonian sensors 1604 are activity or motion sensors, such as, for example, a gyroscope sensor, a vibration sensor, an accelerometer sensor (e.g., a sensor that measures acceleration and de-acceleration), a three dimensional (3D) accelerometer sensor (e.g., sensors that measure the acceleration and de-acceleration and the direction of such acceleration and de-acceleration), a force sensor, a pedometer, a strain gauge, a magnetometer, and a geomagnetic field sensor that may be used for activity level measurements; whereas the physiological sensors 1602 may be used for specific physiological measurements.

In one embodiment, an environmental measurement may be any measurement of an area approximate or adjacent a user. The environmental sensors 1605 may be a humidity sensor, an ambient temperature sensor, an altitude sensor, a barometer, and so forth. A location measurement may be any measurement of a location of the user or a movement of the user. The location sensor 1606 may be a global positioning system (GPS), a triangulation system, or a location sensor. One or a combination of the physiological data 1624, the environmental data 1626, the Newtonian data 1628, the profile data 1630, and the location data 1632 may be obtained from other sources such as through network from sources reachable in the cloud or online.

In another embodiment, the environmental measurement can be any measurement of a local or central location measurement of where a user is located. For example, one or more environmental sensors 1605 may be located ala a location within a threshold radius of the user, such as a threshold radius from the user location. In this example, the environmental sensors 1605 can take environmental measurements and relay the information to the electronic device 1600 or to a communication hub that has a communication channel established with the electronic device 1610. Alternatively, the environmental sensors 1605 can take environmental measurements and relay the information to a processing hub that can analyze the environmental measurements to determine selected environmental factors (such as a humidity level, a heat index, and so forth) and can communicate the environmental factors to the electronic device 1600 or to another electronic device. In another embodiment, the processing hub can receive the environmental measurements from the environmental sensors 1605 and other measurements (such as physiological measurements) from the electronic device 1610. The processing hub can analyze the environmental measurements and the other measurements to determine selected result data, such as a hydration level of a user or a health level of the user. In another embodiment, the electronic device 1600 can take a first set of environmental measurements and the local environmental sensors 1605 can take a second set of environmental measurements. The first set of environmental measurements and the set of environmental measurements can be combined or aggregated and the processing hub and/or the electronic device 1600 can analyze the aggregated environmental measurements.

In another embodiment, the environmental measurements can be from an environmental information outlet or provider. For example, the environmental information outlet or provider is a weather station, a news station, a television station, an online website, and so forth. The electronic device 1600 or the processing hub can receive the environmental information from the environmental information outlet or provider can use the environmental information to determine selected physiological and/or environmental data or factors.

The first sensor interface 1607 may be coupled with the one or more physiological sensors 1602, a second sensor interface 1609 may be coupled with the one or more Newtonian sensors 1604, a third sensor interface 1609 may be coupled with the one or more environmental sensors 1605, and a fourth sensor interface 1610 may be coupled with the one or more location sensors 1606. The processing element 1611 may be operable to execute one or more instructions stored in the memory device 1650, which may be coupled with the processor 1603. In some cases, the processing element 1611 and memory device 1650 may be located on a common substrate or on a same integrated circuit die. Alternatively, the components described herein may be integrated in one or more integrated circuits as would be appreciated by one having the benefit of this disclosure. The memory device 1650 may be any type of memory device, including non-volatile memory, volatile memory, or the like. Although not separately illustrated the memory device 1650 may be one or more types of memory configured in various types of memory hierarchies.

The memory device 1650 may store physiological data 1624, such as current and past physiological measurements, as well as profile data 1630, including user profile data, bibliographic data, demographic data, and the like. The physiological data 1624, and in some cases the profile data 1630, may also include processed data regarding the measurements, such as statistical information regarding the measurements, as well as data derived from the measurements, such as predictive indicators, results, and/or recommendations.

In one example, the profile data 1630 may also include information connected to user profiles of the users that wear the electronic device 1610, such as a gender of the user, an age of the user, a body weight or mass of the user, a health status of the user, a fitness level of the user, or a family health history of the user. In another example, the profile data 1630 can include occupational information of the users that wear the electronic devices 1610, such as a job type, a job title, whether the job is performed indoors or outdoors, a danger level of the job, and so forth. For example, the job types can include an elderly live-at-home job, an oil driller, a construction worker, a railroad worker, a coal mine worker, a job in confined spaces, a fireman, a construction worker, an outdoor worker, an office worker, a truck driver, a child, or a disabled individual.

In one example, the electronic device 1600 can receive the profile data 1630 via a touch screen device integrated into the electronic device 1600 or coupled to the electronic device 1610. In another example, the electronic device 1600 can receive the profile data 1630 via a communication port of the electronic device 1610. For example, the electronic device 1600 can receive profile data 1630 from another device via a wired communication connection (e.g., a universal serial bus) or via a wireless communication connection (e.g., a Bluetooth® communication technology).

The profile data 1630 may also be linked to various physiological data 1624 and Newtonian data 1628 and be tracked over time for the users. The profile data 1630 may also include baselines of physiological parameters for respective users. In one example, the baselines are of a heart rate, a blood pressure, bio-impedance, skin temperature, oxygen levels, hydration levels, electrolyte levels and so forth. When the baselines are included with the user profiles, the user profiles may be referred to as baseline profiles for the respective users.

The memory device 1650 may also store one or a combination of the environmental data 1626, the Newtonian data 1628, the profile data 1630, and the location data 1632. The Newtonian data 1628, environmental data 1626, or location data 1632 may be current and past measurements, as well predictive data for predictive modeling of activity levels, environmental levels, or locations. The memory device 1650 may store instructions of the sensor module 1606 and instructions and data related to the correlator 1613, the baseliner 1615 and the alerter 1617, which perform various operations described below.

In particular, the sensor module 1606 may perform operations to control the physiological sensors 1602, Newtonian sensors 1604, environmental sensors 1605, and location sensors 1606, such as when to turn them on and off, when to take a measurement, how many measurements to take, how often to perform measurements, etc. For example, the sensor module 1606 may be programmed to measure a set of physiological measurements according to a default pattern or other adaptive patterns to adjust when and how often to take certain types of measurements. The measurements may be stored as the physiological data 1624, the environment data 1626, and the Newtonian data 1628, location data 1632, and some of them may also be integrated as a part of the profile data 1630, as discussed.

In the depicted embodiment, the processing element 1608 (e.g., one or more processor cores, a digital signal processor, or the like) executes the instructions of the sensor module 1606 and those related to the correlator 1613, the baseliner 1615, the alerter 1617 and possibly other modules or routines. Alternatively, the operations of the sensor module 1606 and the correlator 1613, the baseliner 1615, and the alerter 1617 may be integrated into an operating system that is executed by the processor 1603. In one embodiment, the processing element 1611 measures a physiological measurement via the first sensor interface 1607. The processing element 1611 may measure an amount of activity of the electronic device 1600 via the second sensor interface 1609. The amount of activity could be movement or motion of the electronic device 1600 (e.g., by tracking location), as well as other measurements indicative of the activity level of a user, such as heart rate, body temperature, skin luminosity, or the like. The processing element 1611 measures an environmental measurement via the third sensor interface 1609. The processing element 1611 measures a location measurement via the fourth sensor interface 1610.

In one embodiment, the Newtonian sensors 1604 may include a hardware motion sensor to measure at least one of movement or motion of the electronic device 1610. The processing element 1611 may determine the amount of activity based the movement or motion of the electronic device 1610. The hardware motion sensor may be an accelerometer sensor, a gyroscope sensor, a magnetometer, a GPS sensor, a location sensor, a vibration sensor, a 3D accelerometer sensor, a force sensor, a pedometer, a strain gauge, a magnetometer, and a geomagnetic field sensor.

The processor 1603 may further execute instructions to facilitate operations of the electronic device 1600 that receive, store and analyze measurement data, environmental data, location data, and profile data. The indicator(s) 1618 may include one or more of a light, a display, a speaker, a vibrator, and a touch display, useable to alert the user to take actions in response to trending levels of: physiological parameters during or after physical activity and/or prepare for undertaking anticipated physical activity; environmental parameters; activity parameters, or location parameters.

In some embodiments, for example, the correlator 1613 may analyze measurement data to correlate physiological data, environmental data, activity data, location data, or user experienced feedback with a physiological parameter, environmental parameter, activity parameter, a location parameter, or user experienced feedback to predict a change in a level of the physiological parameter, environmental parameter; activity parameter, or a location parameter. In one embodiment, the user experienced feedback can be physiological or psychological symptoms experienced by the user. For example, the physiological or psychological symptoms can include: headaches, dizziness, tiredness, mental fatigue, increased thirst, dry mouth, swollen tongue, physical weakness, confusion, sluggishness, and so forth.

Such prediction may enable timely and accurate recommendations to a user in terms of hydrating, adjusting effort levels or other specific actions to address a trend or a change in the physiological parameter, the environmental parameter, the activity parameter, or the location parameter. The recommendations may be displayed in the display 1680, sent via an alert through one of the indictor(s) 1618 or displayed in another device such as a smart phone or tablet or other computing device.

In another embodiment, the correlator 1613 may also track and analyze Newtonian data of the user related to physiological or determined parameters (such as heart rate, oxygenation, skin luminosity, hydration, and the like), related to location and type of activity (such as activity levels associated with being at the gym, riding a bike, attending class, working at a desk, sleeping, or driving in traffic, and the like) and/or related to scheduling information (such as appointments on a calendar, invites received from friends, or messages related to travel and/or activity plans, and the like). Through this analysis, the electronic device 1600 may track activity data over time, intelligently and continuously (or periodically) analyze all of this information, and alert the user through the indicator(s) 1618 to take a specific action at a proper time before a start of a dehydration condition. The specific action may include to hydrate extra hours before physical activity and to eat at least two hours before any physical activity, or other such timing that may be general to most users, or customized to a training or nutrition routine of a specific user.

In another embodiment, the correlator 1613 can build an individualized profile for the user. The correlator 1613 can receive the individualized profile information from an input device of the electronic device 1610. For example, the correlator 1613 can receive the individualized profile information from a touch screen of the electronic device 1610. In another example, the correlator 1613 can receive the individualized profile information from a device in communication with the electronic device (such as via a USB port or using a Bluetooth® technology). In another embodiment, the electronic device 1600 can include a memory that stores the individualized profile information for the user.

The individualized profile can include physiological information associated with the user. For example, the physiological information can include a hydration condition, an average heart rate of the user, an age of the user, a health level of the user, and so forth. The individualized profile can also include information associated with a location or environment that the user is located. For example, the individualized profile can include: humidity level information, such as when the user is located in a dry climate or in a humid climate; altitude level information, such as when the user is located at a relatively high altitude or a relatively low altitude; seasonal information, such as if it is winter where the user is located or summer. The correlator 1613 can also determine an environmental effect on the user for the location where the user is located at. For example, if the user is located at their home that is at a high altitude with a dry climate and it is a winter season, the correlator 1613 can determine that the user is acclimated to high altitudes, dry climates, and the winter season. The correlator 1613 can also update the user profile when the user changes location. For example, when the user leaves their home location and goes on a vacation to a location that is at a low altitude, a humid climate, and it is a summer season, the correlator 1613 can determine that the user is not acclimated to the low altitude, humid climate, and summer season.

In one embodiment, the electronic device 1600 can alert the user of the changes to the individualized profile. In another embodiment, the electronic device 1600 can alert the user of the changes to effects associated with the changes to the individualized profile. For example, the electronic device 1600 can access a table of predetermine effects of the user changing their user profile. In one example, the table can indicate that when the user switches from a low altitude to a high altitude location, the user may experience altitude sickness. In another example, the table can indicate that when the user switches from a dry climate to a humid climate location, an ability of the user's body to cool itself down when an ambient temperature is relatively high. In another embodiment, the table can indicate when the current user profile indicates safety risks or physiological performance changes.

In another embodiment, the individualized profile can also include information associated with clothing or apparel worn by the user of the electronic device 1610. For example, the individualized profile can indicate that a user may wear different types of apparel for different environments including: a thickness of fabric; a type of a fabric, such as wool or cotton; a number of clothes layers worn by the client; accessories worn by the client, such as hard hats, steeled toed shoes, safety googles, safety belts, and so forth; and gender types of apparel, such as women and men's apparel. In one example, the correlator can adjust measurement information or measurement results based on the different types of clothing or apparel. For example, the correlator 1613 can determine that the user is a firefighter and is wearing multiple layers of clothing to protect against fire. In this example, the correlator 1613 can determine that a cause of a hydration level of the user decreasing is the multiple layers of clothing cause the firefighter to sweat more and loss more fluid than a typical number of layers of clothing worn by the user.

In one embodiment, the alerter 1617 may decide the most appropriate timing and mode of alert, whether through one of the indicator(s) 1618, the display 1680 or another device such as a smart phone, tablet or the like. The type of indicator used to alert the user may also be customized to or by the user.

In one embodiment, the correlator 1613 may determine a correlation between different data points or data sets of the input data (such as data collected from different sensors, devices, or obtained from the cloud or online). The correlator 1613 may determine different types of correlations of the data points or data sets. In one example, the correlator 1613 may execute a Pearson product moment correlation coefficient algorithm to measure the extent to which two variables of input data may be related. In another example, the correlator 1613 may determine relations between variables of input data based on a similarity of rankings of different data points. In another example, the correlator 1613 may use a multiple regression algorithm to determine a correlation between a data set or a data point that may be defined as a dependent variable and one or more other data sets or other data points defined as independent variables. In another example, the correlator 1613 may determine a correlation between different categories or information types in the input data.

In further examples, when the correlator 1613 determines a correlation between the different data points or data sets, the correlator 1613 may use the correlation information to predict when a first event or condition may occur based on a second event or condition occurring. In another example, when the correlator 1613 determines a correlation between the different data points or data sets, the correlator 1613 may use the correlation information to determine a hydration condition. As discussed in the preceding paragraphs, a hydration can be an event that negatively impacts a user's safety or health. In another example, when the correlator 1613 determines a correlation between the different data points or data sets, the correlator 1613 may use the correlation information to determine a cause of a condition and/or event, such as a hydration condition.

Additionally, or alternatively, the correlator 1613 may determine a correlation between physiological data 1624, environmental data 1626, Newtonian data 1628, profile data 1630, and location data 1632. For example, the input data may include hydration level data (physiological data) and ambient temperature data (environmental data). In this example, the correlator 1613 may identify a correlation between an increase in the ambient temperature, a decrease in a hydration level of a user, and a heat stroke. The correlator 1613 may identify the correlation between the ambient temperature, the hydration level, and the heat stroke by using a regression algorithm with the heat stroke as an independent variable and the ambient temperature and the hydration level as dependent variables. When the correlator 1613 has identified the correlation between the heatstroke, the ambient temperature, and the hydration level, the correlator 1613 may predict a heatstroke based on a change in a hydration level of a user or a rate of change of a hydration level of a user and a change in the ambient temperature or a rate of change in the ambient temperature.

Additionally, or alternatively, the correlator 1613 may determine a correlation between a fatigue event, an altitude level, and an oxygenation level of a user. For example, the correlator 1613 may determine a correlation between an increase in the altitude level, a decrease in the oxygenation level of the user, and an increase in a fatigue event. When the correlator 1613 determines the correlation between the altitude level, the oxygenation level, and the fatigue event, the correlator 1613 may predict an increase or decrease in a probability of a hydration condition change based on a change in the oxygenation level of user and the altitude level at which the user is currently at. In one example, the correlator 1613 can use the individualized profile information (as discussed in the preceding paragraphs) of the user to determine the predicted increase or decrease in the probability of a hydration condition change. For example, the correlator 1613 can determine a change in altitude level of the user from a relatively low altitude to a relatively high altitude. The correlator 1613 can use the individualized profile information to determine that the user is acclimated to the relatively high altitude (such as if they live at a high altitude) and adjust the predicted increase or decrease in the probability of a hydration condition change for the change in altitude in view of the individualized profile information. For example, the correlator 1613 can predict that the change from the low altitude to the high altitude will not increase or decrease the probability of a user becoming dehydrated.

In a further example, the correlator 1613 may identify a correlation between location information and physiological data of a user. For example, the correlator 1613 may determine a location of a user for at a period of time, such as by using GPS sensor data or triangulation sensor data. In this example, the correlator 1613 may receive physiological measurement data (such as heart rate measurement data, optical spectroscopy data, hydration level measurement data, blood pressure measurement data, and so forth). The correlator 1613 may correlate the location of the user with the physiological measurement data to increase an accuracy of data analysis, a diagnosis, or result data and/or provide additional details regarding a cause of a change in a hydration condition.

In one example, the correlator 1613 may determine that a user is at work in an office location. When the correlator 1613 detects an increase in a heart rate or a blood pressure of a user, the correlator 1613 may correlate heart rate or blood pressure data and the location information to determine a cause of the cognitive ability reduction event. For example, when a heart rate or blood pressure of an individual increases while at a work in an office, the correlator 1613 may determine that the heart rate or blood pressure increase may be due to psychological causes (such as stress) rather than physiological causes (such as exercising or working out) because the user is at a location where an individual is not likely to physically exert himself or herself.

In another example, the correlator 1613 may determine an occupation of the user, such as by using the profile data 1630. In one embodiment, the correlator 1613 can determinate that the occupation of the user is a higher risk occupation (e.g., a statistically more dangerous occupation). For example, the correlator 1613 can access a database or list (stored at the memory device 1650 or externally) that includes information associated with an occupation, such as environmental exposure. When the correlator 1613 detects that the occupation of the user is a higher risk occupation (e.g., an occupation with a risk level that exceeds a threshold value), the correlator 1613 may correlate heart rate data, blood pressure data, hydration level data, with the occupational information to determine a cause of a hydration condition change. For example, when a heart rate and blood pressure of an individual increases and a hydration level of the individual decreases while the individual is working at an oil refinery or on a farm, the correlator 1613 may determine that the heart rate or blood pressure increase may be due to physiological influences of the occupation (such as strenuous labor or no breaks) rather than psychological causes (such as stress) because the occupation where the individual is working at is likely to include physical exertion.

In a further example, the correlator 1613 may use a multiple regression algorithm to determine a correlation between multiple data points or data sets and a hydration condition. For example, the correlator 1613 may receive heart rate data, skin temperature, bio-impedance data, skin luminosity and hydration level data of a user. In this example, the correlator 1613 may determine a correlation between these types of physiological data and a dehydration event of the individual. For example, the physiological data could be from optical spectroscopy (skin luminosity) and/or bio-impedance data. The correlator 1613 may then determine that as the bio-impedance of an individual increases and skin luminosity decreases, a probability of a dehydration event occurring increases.

Additionally, or alternatively, the correlator 1613 may filter out a correlation determination (e.g., a determination that data points or data sets and a hydration condition may be correlated) when a correlation level is-below a threshold level. For example, when the correlator 1613 determines that there may be a 30 percent correlation between a skin temperature or abio-impedance level of an individual and a fall event, the correlator 1613 may filter out or disregard the correlation information when determining a cause of the fall event. In another example, the correlator 1613 can use a learning algorithm or machine learning to determine when to filter out a correlation determination. For example, at a first instance of a fall, there may be a 30 percent correlation between a skin temperature or abio-impedance level of an individual and a fall event The correlator 1613 can monitor multiple fall events and use machine learning to determine that the initial 30 percent correlation is actually a 60 percent correlation and adjust the filter to not filter out the correlation between the skin temperature or the bio-impedance level of an individual and a fall event or assign the correlation of the skin temperature or the bio-impedance level of an individual and a fall event a different weight.

Additionally, or alternatively, the correlator 1613 may filter out the correlation determination based on a schedule of an individual. For example, when the correlator 1613 determines that an individual is taking a lunch break, off of work, or sleeping, the correlator 1613 may filter out environmental conditions that are associated with the occupation of the user, e.g., the correlator 1613 can filter out false positives.

Additionally, or alternatively, the correlator 1613 may discount or weight a correlation determination based on the correlation level of the correlation determination. For example, when the correlator 1613 determines that there may only be a 30 percent correlation between an occupation of an individual and a hydration level of an individual, the correlator 1613 may discount or assign a lower weight to the correlation determination (relative to a higher correlation percentage such as 90 percent) when determining a change in hydration condition.

Additionally, or alternatively, the correlator 1613 may assign weights to different factors, such as: physiological data 1624 (e.g., different types or qualities of physiological parameters), environmental data 1626 (e.g., different types or quality of environmental parameters), Newtonian data 1628 (e.g., different types or quality of Newtonian parameters), profile data 1630, location data 1632 (e.g., different types or quality of location parameters), a time of day, and so forth. In one example, the correlator 1613 may assign a first weight to hydration level data of an individual and a second weight to profile data of an individual when determining a probability of a change in hydration condition for an individual. In this example, when determining the probability of a change in a hydration condition, the correlator 1613 may assign a higher weight to the hydration level data relative to the profile data, for example.

The correlator 1613 may additionally, or alternatively, use predetermined weights for the physiological data 1624, environmental data 1626, Newtonian data 1628, profile data 1630, and location data 1632. In another example, the correlator 1613 may receive user defined or predefined weights from an input device indicating the weights for the different physiological and/or environmental data. In another example, the correlator 1613 may determine the weights to assign to the physiological data 1624, environmental data 1626, Newtonian data 1628, profile data 1630, and location data 1632 based on correlation levels of the physiological data 1024, environmental data 1626, Newtonian data 1628, profile data 1630, and location data 1632. For example, when a correlation level between a hydration condition and a heart rate of an individual may be relatively low over a threshold period of time and/or under a threshold number of different conditions, the correlator 1613 may assign a low weight to heart rate data when determining a cause of a change in hydration condition.

In one example, the correlator 1613 may assign different weights to one or more of the physiological data 1624, environmental data 1626, Newtonian data 1628, profile data 1630, and location data 1632 based on other physiological data 1624, environmental data 1626, Newtonian data 1628, profile data 1630, and location data 1632. For example, based on a location of an individual, the correlator 1613 may assign a first weight to environmental data 1626 and a second weight to profile data 1630. In another example, the correlator 1613 may assign weights to different hydration conditions.

The invention claimed is:

1. A device, comprising:
   a housing comprising:
      an outer surface that defines a first side of the housing and a second side of the housing, wherein the first side of the housing is an underside of the housing shaped to be affixed to a body of a user; and
      an inner cavity that houses electronic components;
   an impedance sensor, comprising:
      a first contact terminal disposed adjacent to the outer surface; and
      a second contact terminal disposed adjacent to the outer surface and separated by a fixed distance from the first contact terminal, the fixed distance ranging from 7 millimeters (mm) to 60 mm;
   a sensor interface positioned in the inner cavity of the housing and electronically coupled to the impedance sensor, wherein the sensor interface is configured to:
      generate an electric signal by the first contact terminal;
      receive the electric signal from the second contact terminal through a skin layer below a surface of the body of the user; and
      determine an impedance measurement between the first contact terminal and the second contact terminal based on the electric signal;
   a processing device electronically coupled to the sensor interface or the impedance sensor, wherein the processing device is configured to determine, based on the impedance measurement:
      a condition of a vascular system of the user;
      an amount of a constituent of the vascular system of the user; or
      a hydration condition of the user; and
   a non-conductive material adjacent to and positioned between the first contact terminal and the second contact terminal, wherein the non-conductive material prevents a portion of the electric signal that has been transmitted from the first contact terminal and that has not entered the body of the user from reaching the second contact terminal.

2. The device of claim 1, wherein the first contact terminal or the second contact terminal is:
   flush with the outer surface;
   recessed within the housing relative to the outer surface; or
   extends away from the outer surface and the housing.

3. The device of claim 1, wherein:
   the fixed distance is greater than 25 mm;
   the fixed distance ranges from 7 mm to 12 mm;
   the fixed distance ranges from 12 mm to 18 mm;
   the fixed distance ranges from 20 mm to 30 mm; or
   the fixed distance ranges from 30 mm to 60 mm.

4. The device of claim 1, wherein the processing device is further configured to determine an amount or identity of the constituent based on a difference between the electric signal generated by the first contact terminal and the electric signal received by the second contact terminal.

5. The device of claim 1, wherein the first contact terminal or the second contact terminal has a surface area of contact with the surface of the body of the user ranging from 3 $mm^2$ to 5 $mm^2$.

6. The device of claim 1, wherein the non-conductive material comprises glass, porcelain, plastic, or rubber.

7. A method, comprising:
   transmitting, by a first impedance pad, an electric current into a body of a user;
   detecting, by a second impedance pad, a portion of the electric current from a depth below a surface of the body, wherein the first impedance pad and the second impedance pad are separated by a fixed distance, the fixed distance ranging from:
      1 mm to 4 mm and the depth extends up to an epidermal layer of the body;
      12 mm to 18 mm and the depth extends up to a dermal layer of the body; or 20 mm to 30 mm and the depth extends into a vascular system of the body;
wherein a non-conductive material is located adjacent to and positioned between the first impedance pad and the second impedance pad, wherein the non-conductive material prevents a portion of the electric current that has been transmitted from the first impedance pad and that has not entered the body of the user from reaching the second impedance pad;
determining, by a processing device communicatively coupled to the first impedance pad or the second impedance pad, a current impedance measurement of the body;
comparing, by the processing device, the current impedance measurement of the body to a previous impedance measurement;
determining, by the processing device, a hydration condition of the user has changed when the current impedance measurement of the user is different than the previous impedance measurement; and
communicating to the user, by a user device communicatively coupled to the processing device, that the hydration condition of the user has changed.

8. The method of claim 7, wherein the fixed distance is selected based on a surface area of the first impedance pad or the second impedance pad, wherein the surface area ranges from 3 $mm^2$ to 5 $mm^2$.

9. The method of claim 7, wherein the current impedance measurement is based at least in part on:
a strength of the portion of the electric current detected by the second impedance pad; or
a speed at which the portion of the electric current detected by the second impedance pad travels between the first impedance pad and the second impedance pad.

10. The method of claim 7, further comprising:
in response to the current impedance measurement being more than the previous impedance measurement, determining, by the processing device, skin of the user is becoming dry; and
in response to the current impedance measurement being less than the previous impedance measurement, determining, by the processing device, the user is perspiring,
wherein determining whether the hydration condition of the user has changed is based at least in part on whether the skin of the user is becoming dry or whether the user is perspiring.

11. The method of claim 7, wherein determining whether the hydration condition of the user has changed comprises determining the user is becoming more hydrated when the current impedance measurement is less than a normal skin impedance level for the user.

12. The method of claim 7, wherein determining whether the hydration condition of the user has changed comprises determining the user is becoming dehydrated when the current impedance measurement is more than a normal skin impedance level for the user.

13. The method of claim 7, further comprising placing sweat, electrocardiogram gel, water, or spit between the first impedance pad and skin of the user or between the second impedance pad and the skin of the user, wherein the sweat, electrocardiogram gel, water, or spit eliminates air resistances between the first impedance pad or the second impedance pad and the skin of the user.

14. A method, comprising:
transmitting, by a first impedance pad, an electric current into a body of a user;
detecting, by a second impedance pad, a portion of the electric current from a depth below a surface of the body, wherein a distance between the first impedance pad and the second impedance pad is between 7 millimeters (mm) and 60 mm;
determining, by a sensor interface communicatively coupled to the first impedance pad or the second impedance pad, a current impedance measurement of the body;
determining, by a processing device communicatively coupled to the sensor interface, a current hydration condition of the user based on the current impedance measurement;
comparing, by the processing device, the current impedance measurement to a previous impedance measurement corresponding to an operating hydration condition of the user, wherein the operating hydration condition comprises a range of normal hydration conditions for the user;
in response to the current impedance measurement being greater than the previous impedance measurement, determining, by the processing device, a current hydration condition of the user is hypo-hydration;
in response to the current impedance measurement not being greater than the previous impedance measurement, determining, by the processing device, a current hydration condition of the user is not hypo-hydration;
in response to the current impedance measurement not being greater than the previous impedance measurement and being less than the previous impedance measurement, determining, by the processing device, a current hydration condition of the user is hyper-hydration;
in response to the current impedance measurement not being greater than the previous impedance measurement and not being less than the previous impedance measurement, determining, by the processing device, the current hydration condition of the user is euhydration, wherein euhydration comprises a range of hydration levels of the user; and
determining a contact impedance between the first impedance pad or the second impedance pad and the surface of the body, wherein:
the contact impedance is determined not to factor into the current impedance measurement when the current impedance measurement is less than 1,000 ohms; and
the contact impedance is determined to be a factor in the current impedance measurement when the current impedance measurement ranges from 1,000 ohms to 20,000 ohms; and
notifying the user the contact impedance is interfering with correct measurement of the current hydration condition of the user.

15. The method of claim 14, wherein the operating hydration condition is determined from a set of previous hydration conditions of the user that establish a euhydration condition of the user.

16. The method of claim 14, further comprising determining a contact impedance between the first impedance pad or the second impedance pad and the surface of the body is due to debris accumulating in pores in the first impedance pad or the second impedance pad when use of a conductive solution between the first impedance pad or the second impedance pad and the surface of the body does not decrease the current impedance measurement to less than 1,000 ohms.

17. The method of claim 14, wherein a spacing between the first impedance pad and the second impedance pad is selected based on a part of the body of the user where the current impedance measurement is to be taken.

18. The method of claim 17, wherein the spacing ranges from:
- 7 mm to 12 mm when the part of the body of the user is a finger tip;
- 12 mm to 18 mm when the part of the body of the user is a wrist;
- 20 mm to 30 mm when the part of the body of the user is a vascular system of the wrist; or
- 30 mm to 60 mm when the part of the body of the user is a bicep or a thigh.

* * * * *